US012527906B2

(12) United States Patent
DuBois et al.

(10) Patent No.: US 12,527,906 B2
(45) Date of Patent: Jan. 20, 2026

(54) DEVICE FOR TREATING BLEEDING

(71) Applicant: Teleflex Life Sciences LLC, Wilmington, DE (US)

(72) Inventors: Brian R. DuBois, Redwood City, CA (US); Luke Christopher Raymond, Redwood City, CA (US); Wei Liang, Redwood City, CA (US); Vladimir Gusiatnikov, Redwood City, CA (US); Johan Oscar Lennart Andreasson, Redwood City, CA (US); Bang Quoc Vu, Redwood City, CA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 271 days.

(21) Appl. No.: 17/283,844

(22) PCT Filed: Nov. 8, 2019

(86) PCT No.: PCT/US2019/060614
§ 371 (c)(1),
(2) Date: Apr. 8, 2021

(87) PCT Pub. No.: WO2020/097560
PCT Pub. Date: May 14, 2020

(65) Prior Publication Data

US 2021/0379276 A1 Dec. 9, 2021

Related U.S. Application Data

(60) Provisional application No. 62/757,270, filed on Nov. 8, 2018.

(51) Int. Cl.
*A61M 3/02* (2006.01)

(52) U.S. Cl.
CPC ......... *A61M 3/0258* (2013.01); *A61M 3/0202* (2021.05); *A61M 3/0245* (2013.01)

(58) Field of Classification Search
CPC .............. A61M 3/0258; A61M 3/0283; A61M 3/0295; A61M 2205/273;
(Continued)

(56) References Cited

U.S. PATENT DOCUMENTS

| | | | | | |
|---|---|---|---|---|---|
| 2,908,273 | A * | 10/1959 | Huston | A61M 3/022 | 604/35 |
| 4,637,814 | A * | 1/1987 | Leiboff | A61M 3/0283 | 604/27 |

(Continued)

FOREIGN PATENT DOCUMENTS

| | | | |
|---|---|---|---|
| CN | 2540980 | | 3/2003 |
| CN | 105852938 | A | 8/2016 |

(Continued)

OTHER PUBLICATIONS

Eryilmaz, Aylin et al. "Our Approach to Adult Patients With Epistaxis," J Craniofacial Surgery, 27(3): e298-e301 (May 2016).

(Continued)

*Primary Examiner* — Kami A Bosworth
*Assistant Examiner* — Avery Smale
(74) *Attorney, Agent, or Firm* — Dorsey & Whitney LLP

(57) ABSTRACT

A system for treating internal bleeding via application of a heated irrigant, such that the heated irrigant is delivered at a flow rate of between 2 cc/s and 12 cc/s and at a temperature of between 46 degrees Celsius and 52 degrees Celsius.

11 Claims, 15 Drawing Sheets

(58) Field of Classification Search

CPC .. A61M 2205/3334; A61M 2205/3368; A61M 2205/3653; A61M 2205/50; A61M 2210/0618; A61M 2210/1053; A61M 2210/1089; A61M 3/0202; A61M 3/02; A61M 3/0245; A61M 1/77; A61M 1/772; A61M 1/774; A61M 3/0204; A61M 3/0233; A61M 3/0254; A61M 3/0279; A61M 25/007; A61B 18/04; A61F 7/0085

See application file for complete search history.

(56) References Cited

U.S. PATENT DOCUMENTS

| | | | | | |
|---|---|---|---|---|---|
| 4,924,851 | A | | 5/1990 | Ognier et al. | |
| 5,178,606 | A | * | 1/1993 | Ognier | A61M 1/77 604/114 |
| 5,499,994 | A | | 3/1996 | Tihon et al. | |
| 5,546,964 | A | | 8/1996 | Stangerup | |
| 6,077,246 | A | * | 6/2000 | Kullas | A61M 1/72 417/477.2 |
| 6,228,048 | B1 | * | 5/2001 | Robbins | A61M 3/0279 604/27 |
| 9,211,381 | B2 | * | 12/2015 | Faries | A61M 5/44 |
| 9,931,192 | B2 | | 4/2018 | McLean et al. | |
| 9,949,321 | B1 | | 4/2018 | Khanifar et al. | |
| 10,349,998 | B2 | | 7/2019 | Levin et al. | |
| 10,702,261 | B2 | | 7/2020 | Stiggelbout | |
| 2003/0135250 | A1 | * | 7/2003 | Lauman | H05B 3/0085 607/104 |
| 2003/0229263 | A1 | | 12/2003 | Connors et al. | |
| 2004/0181235 | A1 | | 9/2004 | Daignault et al. | |
| 2005/0008354 | A1 | | 1/2005 | Cassidy | |
| 2005/0256530 | A1 | | 11/2005 | Petros | |
| 2006/0195008 | A1 | | 8/2006 | Whalen et al. | |
| 2007/0265689 | A1 | * | 11/2007 | Frey | A61M 5/44 607/113 |
| 2008/0262424 | A1 | | 10/2008 | Hooft | |
| 2009/0112234 | A1 | | 4/2009 | Crainich et al. | |
| 2010/0063351 | A1 | | 3/2010 | Witzmann et al. | |
| 2010/0191045 | A1 | | 7/2010 | Gobron et al. | |
| 2010/0217276 | A1 | * | 8/2010 | Garrison | A61B 17/320725 604/9 |
| 2010/0256442 | A1 | | 10/2010 | Ogdahl et al. | |
| 2010/0261950 | A1 | | 10/2010 | Lund et al. | |
| 2010/0286717 | A1 | | 11/2010 | Heinrich et al. | |
| 2011/0082471 | A1 | | 4/2011 | Holcomb et al. | |
| 2011/0105841 | A1 | | 5/2011 | Kutikov et al. | |
| 2011/0172755 | A1 | | 7/2011 | Nelson et al. | |
| 2011/0276081 | A1 | | 11/2011 | Kilemnik | |
| 2012/0041533 | A1 | | 2/2012 | Bertolino et al. | |
| 2012/0041534 | A1 | | 2/2012 | Clerc et al. | |
| 2012/0245600 | A1 | | 9/2012 | McLean et al. | |
| 2012/0265006 | A1 | | 10/2012 | Makower et al. | |
| 2013/0268001 | A1 | | 10/2013 | Catanese et al. | |
| 2013/0296889 | A1 | | 11/2013 | Tong et al. | |
| 2014/0005473 | A1 | | 1/2014 | Catanese et al. | |
| 2014/0031835 | A1 | | 1/2014 | Viker et al. | |
| 2014/0180067 | A1 | | 6/2014 | Stigall et al. | |
| 2014/0275756 | A1 | | 9/2014 | Bender et al. | |
| 2014/0296881 | A1 | | 10/2014 | Ranucci et al. | |
| 2015/0025652 | A1 | | 1/2015 | McLean et al. | |
| 2015/0122294 | A1 | * | 5/2015 | Wang | A61M 3/0258 134/22.12 |
| 2015/0127050 | A1 | | 5/2015 | Lamson et al. | |
| 2015/0351743 | A1 | | 12/2015 | Stiggelbout | |
| 2016/0022265 | A1 | | 1/2016 | Kawaura et al. | |
| 2016/0045297 | A1 | | 2/2016 | Siegel et al. | |
| 2016/0095685 | A1 | | 4/2016 | Vemuri et al. | |
| 2016/0220296 | A1 | | 8/2016 | Hastings et al. | |
| 2017/0000598 | A1 | | 1/2017 | Bachar | |
| 2017/0007310 | A1 | * | 1/2017 | Rajagopalan | A61B 5/4255 |
| 2017/0135830 | A1 | | 5/2017 | Harkin et al. | |
| 2017/0156723 | A1 | | 6/2017 | Keating et al. | |
| 2018/0103945 | A1 | | 4/2018 | Ciulla et al. | |
| 2018/0318114 | A1 | | 11/2018 | Huang et al. | |
| 2019/0029880 | A1 | | 1/2019 | DuBois | |
| 2019/0125334 | A1 | | 5/2019 | Tong et al. | |
| 2020/0038213 | A1 | | 2/2020 | Bly et al. | |
| 2020/0121442 | A1 | | 4/2020 | Askeland | |
| 2021/0145619 | A1 | | 5/2021 | Bly et al. | |
| 2021/0161641 | A1 | | 6/2021 | Bachar | |
| 2021/0161642 | A1 | | 6/2021 | Jen et al. | |
| 2021/0307641 | A1 | | 10/2021 | Rumbles et al. | |
| 2022/0000445 | A1 | | 1/2022 | Datta et al. | |
| 2022/0031357 | A1 | | 2/2022 | Cutts et al. | |
| 2022/0031358 | A1 | | 2/2022 | Yarra et al. | |
| 2022/0031389 | A1 | | 2/2022 | Fischell et al. | |
| 2022/0061834 | A1 | | 3/2022 | Chung et al. | |
| 2022/0125499 | A1 | | 4/2022 | Hoey et al. | |
| 2022/0133462 | A1 | | 5/2022 | Kilemnik | |
| 2022/0142464 | A1 | | 5/2022 | Petroff et al. | |
| 2022/0240925 | A1 | | 8/2022 | Epstein et al. | |
| 2022/0249219 | A1 | | 8/2022 | Chung et al. | |
| 2022/0265262 | A1 | | 8/2022 | Melsheimer | |
| 2022/0273918 | A1 | | 9/2022 | Ghriallais et al. | |
| 2022/0378577 | A1 | | 12/2022 | Anderson et al. | |
| 2022/0394827 | A1 | | 12/2022 | Raymond et al. | |
| 2022/0395363 | A1 | | 12/2022 | Ghriallais et al. | |
| 2023/0022482 | A1 | | 1/2023 | Dhavale | |

FOREIGN PATENT DOCUMENTS

| | | | |
|---|---|---|---|
| CN | 109675177 | A | 4/2019 |
| CN | 211156119 | U | 8/2020 |
| CN | 112891032 | A | 6/2021 |
| CN | 216221843 | U | 4/2022 |
| DE | 102019101987 | A1 | 7/2020 |
| GB | 1563795 | A | 4/1980 |
| JP | 2014502870 | A | 2/2014 |
| JP | 2023502729 | A | 1/2023 |
| KR | 101534820 | B1 | 7/2015 |
| WO | 2012028843 | A1 | 3/2012 |
| WO | 2012084268 | A1 | 6/2012 |
| WO | 2017004432 | A1 | 1/2017 |
| WO | 2020097560 | A1 | 5/2020 |
| WO | 2021091713 | A1 | 5/2021 |
| WO | 2021190092 | A1 | 9/2021 |

OTHER PUBLICATIONS

Novoa, E. et al. "Hot water irrigation as treatment for intractable posterior epistaxis in an out-patient setting," J Laryngology & Otology, 126: 58-60 (2012).

PCT International Search Report mailed Feb. 20, 2020 in Application No. PCT/US2019/060614 filed Nov. 8, 2019.

PCT International Search Report mailed Jan. 21, 2021 in Application No. PCT/US2020/057339 filed Oct. 26, 2020.

PCT Written Opinion mailed Feb. 20, 2020 in Application No. PCT/US2019/060614 filed Nov. 8, 2019.

PCT Written Opinion mailed Jan. 21, 2021 in Application No. PCT/US2020/057339 filed Oct. 26, 2020.

Schlegel-Wagner, Christoph et al. "Non-invasive treatment of intractable posterior epistaxis with hot-water irrigation," Rhinology, 44: 90-93 (2006).

Japanese Office Action mailed Aug. 14, 2023, in JP Patent Application No. 2021-523955.

Stangerup, Sven-Eric et al. "New Modification of Hot-Water Irrigation in the Treatment of Posterior Epistaxis," Arch Otolaryngol Head Neck Surg, vol. 125: pp. 686-690 (Jun. 1999).

Examination Report issued in Europe for European Patent Application No. 19816990.6, dated Oct. 15, 2024, 10 pgs.

Office Action issued in China and its English translation for Chinese Patent Application No. 201980073605.4, dated Nov. 9, 2024, 9 pgs.

Decision for Final Rejection issued in Japan and its English translation, JP Application No. 2021-523955, mailed Feb. 6, 2025, 2 pgs.

Decision of Rejection issued in China and its English translation, CN Application No. 201980073605.4, mailed Jan. 21, 2025, 10 pgs.

* cited by examiner

DEVICE FOR TREATING BLEEDING

CROSS REFERENCE TO RELATED APPLICATIONS

This application is a U.S. national stage application under 35 U.S.C. 371 of PCT Application No. PCT/US2019/060614, entitled "DEVICE FOR TREATING BLEEDING" and filed Nov. 8, 2019, which claims priority to U.S. provisional patent application no. 62/757,270, entitled "DEVICES AND METHODS FOR TREATING EPISTAXIS USING HOT WATER IRRIGATION" and filed on Nov. 8, 2018, each of which is herein incorporated by reference in its entirety.

BACKGROUND OF THE INVENTION

The present invention relates generally to medical devices and methods of use, and more particularly to systems and methods for treating bleeding in a body cavity such as intra-nasal bleeding (epistaxis), bleeding diverticula in the colon, upper gastrointestinal bleeding in the stomach or duodenum, bleeding in the esophagus, bleeding in the uterus, and bleeding in the urethra.

Tamponade treatment for epistaxis is painful and traumatic to the nasal mucosa and may necessitate hospitalization for several days. A posterior pack is placed to occlude the choanal arch and, in conjunction with an anterior nasal pack, provide hemostasis. Posterior packing can be accomplished with gauze, a Foley catheter, a nasal sponge/tampon, or an inflatable nasal balloon catheter. Posterior packing is very uncomfortable and may necessitate procedural sedation. Hot water irrigation was introduced as a treatment of epistaxis 140 years ago. However, its use was abandoned by the middle of the 20th century because many patients were at risk of aspirating water and the development of nasal tampons and advances in lighting and endoscopic techniques replaced the practice of hot water irrigation.

Hot water irrigation treatment for posterior epistaxis involves running hot water into the bleeding nose cavity and the treatment is successful in many cases. The therapeutic temperature of the hot water is from 46 degrees Celsius to 52 degrees Celsius. Water temperatures below 46 degrees Celsius have no effect, only light changes occur at 46 degrees Celsius and 47 degrees Celsius, and the best effect occurs between 48 degrees Celsius and 52 degrees Celsius as vasodilation, edema of the mucosa, and subsequent narrowing of the intranasal lumen occur in this temperature range. Severe changes, including epithelial necrosis, occur when the treatment temperature is higher than 52 degrees Celsius. The hemostatic effect of hot water treatment for epistaxis may be caused by: (1) edema and narrowing of the intranasal lumen, (2) vasodilation of the mucosal vessels, (3) cleaning blood coagulates from the nasal passageway, and (4) elevated temperatures accelerating the clotting cascade. In a study conducted by Stangerup et al in 1999, the treatment proved to be effective, less painful, less traumatic, and required a shorter hospital stay than tamponade treatment.

The study performed by Stangerup et al, included a thermometer (0) degrees Celsius-100 degrees Celsius), a thermo-bucket filled with fresh hot water (50 degrees Celsius) from the hot water tap, a 10-mL and a 100-mL syringe, and the catheter. The patient was instructed to sit with the head flexed and a catheter was introduced via the bleeding nasal cavity. The balloon was then filled with 10 mL of hot water, and the catheter was pulled back so that the balloon on the end of the catheter sealed the posterior choana of the bleeding nasal cavity. The nasal cavity was irrigated forcefully via the catheter with 500 mL of hot water using a 100-ml syringe. After irrigation, the catheter was removed and the patient was observed for 15 minutes.

Although the hot water irrigation treatment used by Stangerup et al was effective in reducing the likelihood of aspirating water by blocking the choana with a balloon, it is not commonly used because it is inconvenient, inconsistent, and time consuming for the care giver.

Benign Prostatic Hyperplasia (BPH), or prostate gland enlargement, is one of the most common medical conditions that affect men, particularly elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

Established minimally invasive procedures for treating BPH symptoms include Transurethral Microwave Thermotherapy (TUMT), Transurethral Needle Ablation (TUNA), and Interstitial Laser Coagulation (ILC). Other newer procedures include steam induced coagulation necrosis of prostate tissue and the use of pressurized water to remove prostate tissue. And certain implants are being used to open the prostatic urethra.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland thus reducing the severity of BPH symptoms.

Another example of a minimally invasive procedure for treating BPH symptoms is Transurethral Needle Ablation (TUNA). In this procedure, heat induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radio-frequency needles that emerge at an angle of 90 degrees from the delivery catheter. The two radio-frequency needles are aligned are at an angle of 40 degrees to each other so that they penetrate the lateral lobes of the prostate. A radio-frequency current is delivered through the radio-frequency needles to heat the tissue of the lateral lobes to 70-100 degrees Celsius at a radio-frequency power of approximately 456 KHz for approximately 4 minutes per lesion. This creates coagulation defects in the lateral lobes. The coagulation defects cause shrinkage of prostatic tissue, which, in turn, reduces the degree of squeezing of the urethra by the prostate gland thus reducing the severity of BPH symptoms.

Another example of a minimally invasive procedure for treating BPH symptoms is Interstitial Laser Coagulation (ILC), In this procedure, laser induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy along the terminal 3 mm of the laser fiber. The distal tip is inserted into the middle lobe of the prostate gland and laser energy is delivered through the distal tip for a desired time. This heats the middle lobe and causes laser induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which in turn causes the prostate gland to shrink. Shrinkage of the prostate gland reduces the degree of squeezing of the urethra by the prostate thus reducing the severity of BPH symptoms.

Although some of these methods can be effective at alleviating symptoms of BPH, these methods frequently create bleeding injury within the prostatic urethra. The bleeding injury can be a result of the intentional destruction, dissection, or penetration of tissue, or it can be incidental to the treatment, such as when a minimally invasive device injures tissue along the prostatic urethra during insertion or removal of the device. In any case, the bleeding injury in the prostatic urethra is unpleasant for the patient and typically requires several days to resolve. The tissue damage frequently results in hematuria (blood in urine) and may require the patient to wear a catheter to drain urine from the bladder for a period of time adequate to allow the urethra to heal.

Methods and devices are described herein to provide convenience, reduce time, and improve patient comfort.

SUMMARY OF THE INVENTION

A method for treating bleeding in the urethra is disclosed herein, wherein an irrigant in the temperature range of 46 degrees Celsius to 52 degrees Celsius is motivated to lavage a patient's urethra via a catheter wherein the irrigant flows to the urethra via the catheter. The method includes an aspect wherein the irrigant flows from the urethra via the catheter. The method includes an aspect wherein the irrigant flow rate is between 2 cc/second and 12 cc/second.

A system for treating bleeding in a urethra is disclosed herein. The system includes an irrigant source, a heating apparatus connected to the irrigant source, wherein the heating apparatus is configured to heat an irrigant as the irrigant flows through the heating apparatus, and a treatment catheter having an irrigant outlet and an irrigant inlet located at a distal portion of a catheter body of the treatment catheter, wherein the irrigant outlet is located farther distally on the catheter body than the irrigant inlet. Alternatively, the positions of the inlet and outlets may be reversed. The system includes an aspect wherein the irrigant flow rate is between 2 cc/second and 12 cc/second. The system includes an aspect wherein the irrigant temperature is between 46 degrees Celsius and 52 degrees Celsius. The system includes an aspect wherein the system includes a pump. The system includes an aspect wherein the heating apparatus includes a heating element that heats the irrigant via a volumetric heating method, such as via the application of radio-frequency energy.

A method for treating a bleeding nasal passageway is disclosed herein, wherein an irrigant in the temperature range of 46 degrees Celsius to 52 degrees Celsius is motivated to flow into the first nasal passageway then past the posterior septal margin and through the contralateral nasal passageway and out the contralateral rare for a sufficient period of time and volume to cause hemostasis of the bleeding nasal passageway. In some aspects of the method, the irrigant flow rate is between 2 cc/second and 12 cc/second.

A device for treating a bleeding nasal passageway is disclosed herein, wherein the device incudes a reservoir capable of holding or receiving an irrigant, a heating system, temperature controller, irrigant pump, and nasal interface wherein the irrigant is heated by the irrigant heating system to a temperature in the range of 48 degrees Celsius to 52 degrees Celsius and the irrigant is motivated by the irrigant pump to flow into a first nasal passageway and past a bleeding site in the nasal passageway or a contralateral nasal passageway. In some aspects of the method, the irrigant flow rate is between 2 cc/second and 12 cc/second.

A method for treating gastric bleeding is disclosed herein, wherein an irrigant in the temperature range of 46 degrees Celsius to 52 degrees Celsius is motivated to lavage a patient's stomach via a conduit inserted into the stomach such as a naso-gastric tube wherein the stomach has one or more bleeding sites and the irrigant flows out of the patient's stomach and flows or is drawn out of the stomach by suction into a collection receptacle. The conduit may contain a single lumen or preferably a plurality of lumens to enable continuous flow into and out of the stomach.

A device for treating gastric bleeding is disclosed herein, wherein the device is comprised of a reservoir capable of holding or receiving an irrigant, a heating system, temperature controller, irrigant pump, and a conduit capable of being placed in the stomach such as a naso-gastric tube wherein the irrigant is heated by the irrigant heating system to a temperature in the range of 46 degrees Celsius to 52 degrees Celsius and the irrigant is motivated by the irrigant pump to lavage a patient's bleeding stomach and the irrigant exits the bleeding patient's stomach and flows through a conduit and into a collection receptacle. The conduit may contain a single lumen or preferably a plurality of lumens to enable continuous flow into and out of the stomach.

Other features and advantages of embodiments of the present system and method will become apparent from the following description, taken in conjunction with the accompanying drawings, which illustrate, by way of example, certain principles of the system and method.

DETAILED DESCRIPTION OF INVENTION

Figure 1:
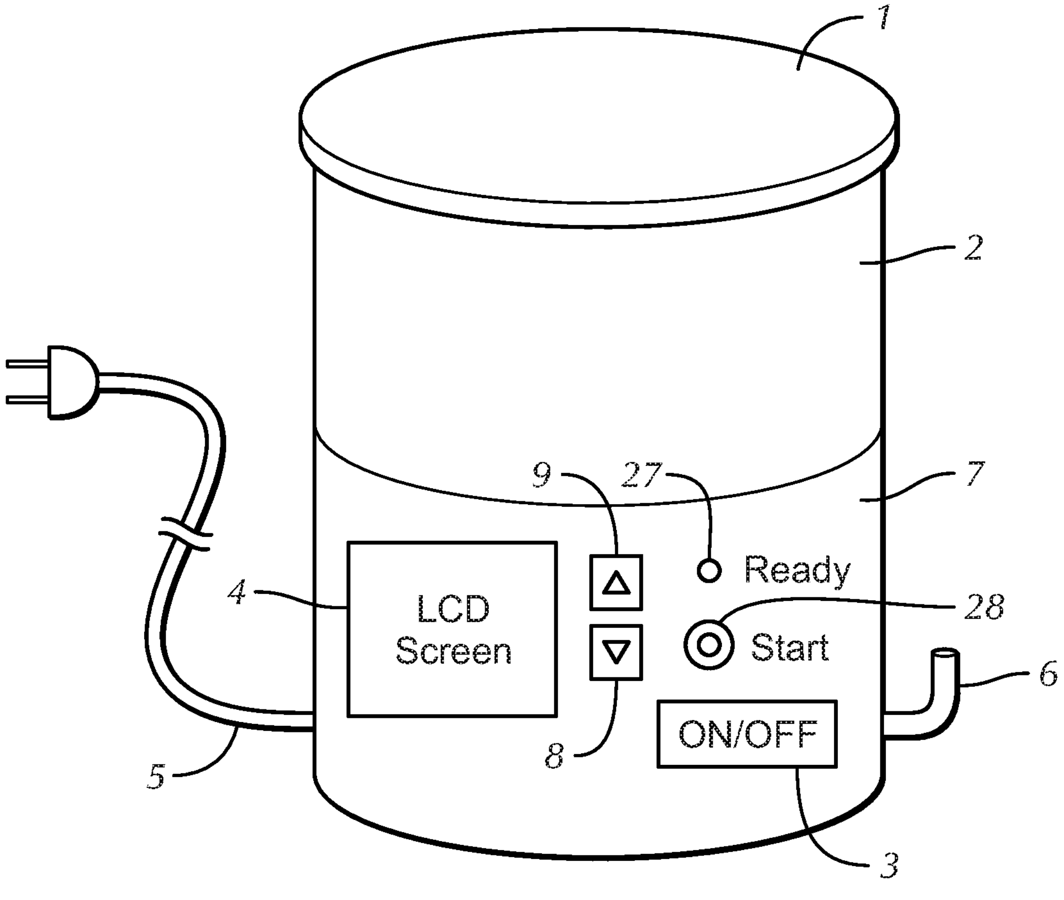
FIG. 1 is a perspective view of an apparatus for heating and pumping an irrigant for treating bleeding according to certain embodiments of the invention.

There is need for improved methods and apparatus for treating a bleeding body cavity, in particular a bleeding nose, stomach, or urethra. The present invention relates to apparatus and methods for arresting bleeding in a body cavity such as intra-nasal bleeding (epistaxis), bleeding diverticula in the colon, upper gastrointestinal bleeding in the stomach or duodenum, bleeding in the esophagus, and bleeding in the uterus. The present invention provides methods and devices for increasing the temperature of body tissues to the proper temperature range that will cause hemostasis. The present invention provides devices and methods for arresting bleeding in a body cavity or passageway.

The size, dimensions, and characteristics of the invention herein may be altered according to the treatment site or body cavity. The device is not limited to any particular body cavity or treatment location.

Irrigant may refer to any number of irrigants including water, saline, or water with solutions such as sodium chloride and sodium bicarbonate. In some embodiments, the actual composition of the irrigant is less important than the temperature and flow rate, as the irrigant acts to raise the temperature of the mucosa for a period of time. Thus, to the extent an irrigant is specified in an embodiment, such as when the use of water is described, it is understood that other irrigants may also be used in such an embodiment.

One method for causing hemostasis is to irrigate the bleeding site with irrigant at a temperature in the range of 46 degrees Celsius to 52 degrees Celsius. In the context of epistaxis, irrigation occurs by causing the irrigant to flow through the nare and nasal passageway toward the choana, around the posterior septal margin, then through the contralateral nasal passageway away from the choana before it exits the contralateral nare. The irrigant may flow toward or away from the choana in the bleeding nasal passageway with only minor differences in efficacy.

Hot water irrigation for treating epistaxis involves motivating irrigant at the therapeutic temperature into the first nare such that it flows through nasal passageway, around the septum and through the second nasal passageway before exiting the second nare. The use of hot water irrigation was almost completely discontinued several decades ago because many patients were at risk for aspirating water into the lungs.

Hot water irrigation for either the nasal passageway or stomach with 48 degrees Celsius to 52 degrees Celsius water may be uncomfortable for the patient unless the amount of heat delivered to the nasal passageway(s) or stomach is controlled. This may be done by conditioning to the high temperature by starting at a lower, more tolerable temperature then increasing the temperature at a tolerable rate until the therapeutic temperature range is met and maintained for the prescribed time. Alternatively, the patient's ability to tolerate the therapy may be improved by controlling the irrigant flow rate through the nasal passageway or stomach. Higher flow rates deliver more heat energy to the tissue whereas lower flow rates deliver less heat energy. Anatomical variations between patients may also necessitate adjustments in the flow rate.

Various options for controlling the flow rate of irrigant include controlling the irrigant pressure, controlling the volumetric change of irrigant at the reservoir, flow rate sensors, or controlling the volume of irrigant through a pumping mechanism.

When treating epistaxis, it is desirable to flush any blood clots out of the nasal passageway. This may be performed by directing the flow of irrigant into the nonbleeding (contralateral) nasal passageway and allowing it to flow out of the bleeding side. After the bleeding nasal passageway is cleaned of clots and other matter, it may be desirable to reverse the irrigant direction to flow into the bleeding passageway. This exposes the bleeding mucosa to irrigant in the therapeutic temperature range without a reduction in the irrigant temperature as heat is lost while the irrigant passes through the nonbleeding, contralateral nasal passageway.

Patient comfort may be improved by initially irrigating the nasal passageway at a temperature below the therapeutic minimum of 46 degrees Celsius or the preferential therapeutic minimum 48 degrees Celsius then increasing the temperature to the therapeutic range. Therefore, a device to automatically adjust the temperature for patient comfort by starting lavage at a comfortable temperature, then increasing and maintaining the temperature to the therapeutic range may be used.

Alternatively, the flow rate of the irrigant may be controlled by starting the irrigant at the therapeutic temperature range at a low flow rate to acclimate the tissue to the heat, then optionally increasing the irrigant flow rate after the patient becomes acclimated to the temperature. This method of control has the advantage of not requiring the irrigant temperature to change which requires a significant amount of energy to heat the irrigant quickly.

It may be desirable to provide the therapeutic effect only on the bleeding nasal passageway rather than both the bleeding and contralateral passageway. Therefore, a device capable of motivating therapeutic irrigant into the bleeding nasal passageway then stopping the flow to allow the irrigant before allowing the irrigant to reverse direction and exit the nare of the bleeding passageway.

In certain situations, it may be desirable to lavage the bleeding nasal passageway by inserting a catheter into the bleeding nasal passageway wherein the catheter is configured to seal the choana such that irrigant flows into the bleeding nasal passageway and exits the nare. The device provides irrigant first at a comfortable temperature and pressure, the device then raises the temperature of the irrigant to the therapeutic temperature, pressure, and volume adequate to provide the therapeutic effect.

One method for reducing the likelihood of water aspiration into the lungs is to configure the device such that the patient holds the head tilted forward to ensure the irrigant flows into the first nare and nasal passageway, around the choana, through the contralateral nasal passageway, and out the contralateral nare and away from the patient.

A device designed to treat epistaxis or upper gastrointestinal bleeding is desirable because patients with either condition typically present to an urgent care center or emergency, department for treatment. There are two types of upper gastrointestinal bleeding, variceal and non-variceal. Variceal bleeding tends to be more diffuse with bleeding from multiple sites in the stomach and is difficult to treat with endoscopic techniques. Non-variceal bleeding is arterial bleeding that tends to be profuse and bleeding from a single site. It is typically treated endoscopically with a variety of technologies. Upper gastrointestinal bleeding is challenging to treat because the blood enters the stomach and disguises the location of bleeding. Therefore, a technology to stop bleeding, and clear blood from the stomach is needed to improve identification of the bleeding site for non-variceal bleeding. Furthermore, a technology to stop variceal bleeding is needed because few therapies are available to treat this condition.

An irrigant therapy heating and pump device includes a reservoir to hold a source of irrigant such as water or saline solution, a pump motor connected to a circulating impeller and/or a pumping impeller, an irrigant heating and temperature control system, irrigant passageways, a power switch, and a valve. A therapy switch controls a valve assembly which when the valve assembly is open, enables a flow of irrigant through the irrigant passageway from the reservoir to exit the nozzle. Therapy interface devices described infra are connected to the nozzle and deliver the therapeutic irrigant to the site where therapy is desired. It is understood that the irrigant may involve other irrigants beside water and saline solution.

Another embodiment includes the features described herein with the addition of an effluent receptacle, and a means to provide suction of effluent from the therapy site into the effluent receptacle.

The irrigant therapy heating and pump devices described herein may optionally include a means for filtration or sterilization of the irrigant.

In one embodiment, a device is provided for treating a bleeding nasal passageway. The device includes the irrigant therapy heating and pump device described herein and a section of tubing connected to the nozzle on the proximal extremity of the tubing and a nasal interface connected to the distal extremity of the tubing. The nasal interface engages an epistaxis patient's flare to deliver therapeutic irrigant to one nasal passageway and out of the contralateral nasal passageway. In the embodiment without the effluent receptacle, the irrigant flows out of the contralateral flare and into a basin or sink. In the embodiment with the effluent receptacle, a second nasal interface is provided wherein the second nasal interface engages the contralateral nare and the therapeutic irrigant is recovered and flows into the effluent receptacle.

Another embodiment utilizing the same components listed herein is configured to motivate the temperature-controlled irrigant into one nasal passageway then abruptly stopping the flow of the irrigant prior to it reaching the choana, then allowing the irrigant to reverse its direction and flow out of the same nare that it entered. This embodiment may include a valve mechanism to allow the effluent to flow into an effluent receptacle rather than flowing retrograde into the irrigant receptacle. This embodiment exposes only one nasal passageway to the therapeutic irrigant. This embodiment has the advantage of exposing only one nasal passageway to the therapeutic irrigant thereby not unnecessarily causing the therapeutic effects in the second nasal passageway.

The present invention solves the problem of epistaxis patients aspirating irrigant by using an apparatus that causes the irrigant to flow around the septum and out of the contralateral nasal passageway without the use of a balloon to block the choana. This is accomplished with an apparatus that induces the patient to flex the head forward during use to cause the outflow of therapeutic irrigant directly into a basin. By positioning the head forward and by controlling the irrigant flow rate within the prescribed therapeutic range, the irrigant flows into the first nasal passageway, around the posterior margin of the septum, into and through the contralateral nasal passageway before exiting the contralateral nare thereby eliminating the risk of aspirating therapeutic irrigant. When the irrigant flow rate is too high, there is a risk of irrigant at least partially flowing into one or both of the Eustachian tubes which may cause patient discomfort. Additionally, when the irrigant flow rate is too high, there is a risk of irrigant at least partially flowing posteriorly through the choana where it may be aspirated by the patient.

Another embodiment of this invention involves an apparatus with two irrigant reservoirs such that irrigant flows in a closed circuit between the two reservoirs. The first reservoir contains irrigant that is pumped within a prescribed flow rate range into the first nasal passageway, past the posterior margin of the septum, then into the contralateral nasal passageway before it flows out the contralateral nare, through tubing and into a second reservoir. The second reservoir is fluidly connected to the first reservoir such that as the irrigant flows out of the first reservoir, air from the second reservoir flows into the first reservoir thereby lowering the pressure in the second reservoir and inducing the irrigant to flow into the second reservoir rather than flowing posterior to the choana where it has an increased likelihood of being aspirated.

Another embodiment is an apparatus described herein that has two heat settings, the first heat setting heats the irrigant to a temperature lower than the therapeutic temperature range of 46 degrees Celsius to 52 degrees Celsius. The second heat setting heats the irrigant to within the therapeutic range of 46 degrees Celsius to 52 degrees Celsius. The first heat setting may be used to condition an epistaxis patient to the sensation of heated water flowing through the nasal passageways prior to increasing the temperature to within the therapeutic range. The temperature change may be done automatically by the apparatus or the patient may manually change a switch position. The lower irrigant temperature setting may also be used to heat the irrigant to a comfortable temperature when using the apparatus to rinse the nasal passageways when epistaxis is not present.

Another embodiment is an apparatus described herein that has two flow rate settings, the first flow rate setting pumps the irrigant at a low flow rate in the range of 2 cc/sec to 6 cc/sec then after a preset time or volume of irrigant flows to the therapy site, a second, higher flow rate commences to hasten the therapeutic effect. The lower flow rate setting may be used to condition an epistaxis patient to the sensation of heated water flowing, through the nasal passageways prior to increasing the flow rate of the irrigant to a more effective therapeutic range. The flow rate change may be done automatically by the apparatus or the patient may manually change a switch position. The lower flow rate setting may also be used to provide a more tolerable therapy for patients who are unable to comply with the higher flow rate therapy or when using the apparatus to rinse the nasal passageways when epistaxis is not present.

One embodiment is a reservoir containing irrigant that is positioned inside a heating medium such as water or a heater to heat the irrigant to the therapeutic temperature. When the irrigant temperature is within the therapeutic range, the reservoir is removed from the heating medium and the irrigant is motivated to flow into the nasal passageways by pouring, pumping, or squeezing the reservoir.

Any method of motivating irrigant flow into or through the nasal passageway may be used in addition to a pump such as the force of gravity or an air pressure differential between the reservoir and effluent. Furthermore, the pump may be powered in any manner such as using electrical power from batteries or from an alternating current source or via a manual pump.

A method of treating epistaxis wherein irrigant heated to the range of 46 degrees Celsius to 52 degrees Celsius is motivated to flow through one nare and its nasal passageway around the nasal septum, through the contralateral nasal passageway and exiting the contralateral nare with a sufficient volume of water to cause hemostasis.

A method of treating epistaxis wherein irrigant heated to the range of 46 degrees Celsius to 52 degrees Celsius is motivated to flow through one nare and its nasal passageway around the nasal septum, through the contralateral nasal passageway and exiting the contralateral nare with a sufficient volume of water to cause hemostasis such that the rate of water flow is controlled to control the amount of heat delivered to the tissue thereby providing a tolerable treatment. This control may be either automatically controlled or patient controlled. If patient controlled, the patient will be able to provide the therapy within the temperature range but may slow the flow of irrigant to provide a more tolerable therapy.

A method for treating bleeding in a nasal cavity is provided including sealing the nares of a user to a device including an associated irrigant passageway in communication with an irrigant reservoir and an irrigant effluent receptacle. The irrigant passageway, reservoir, temperature controller, and irrigant heating element are integrally assembled in the device. The irrigant may be heated and controlled solely in the irrigant passageway or in the irrigant reservoir or it may be heated and controlled in both locations or it may be heated in the reservoir and controlled in the irrigant passageway. The temperature of the irrigant is controlled to be maintained within the therapeutic range of 46 degrees Celsius to 52 degrees Celsius when it flows from the device and into the patient's nare. The irrigant is motivated to flow through the bleeding nasal passageway either by flowing directly through the nare of the bleeding passageway or by entering through the contralateral nare, through the contralateral nasal passageway, around the posterior margin of the nasal septum, and into the bleeding nasal passageway before flowing out of the nare.

Another method of treating bleeding in a nasal cavity is provided including sealing the nare of a bleeding nasal passageway to a device including an associated irrigant passageway in communication with an irrigant reservoir and an irrigant effluent receptacle. The irrigant passageway, reservoir, temperature controller, and irrigant heating element are integrally assembled in the device. The irrigant may be heated and controlled solely in the irrigant passageway or in the irrigant reservoir or it may be heated and controlled in both locations or it may be heated in the reservoir and controlled in the irrigant passageway. The temperature of the irrigant is controlled to be maintained within the therapeutic range of 46 degrees Celsius to 52 degrees Celsius when it flows from the device and into the patient's nare in the bleeding passageway. The irrigant is motivated to flow into the bleeding nasal passageway, then stops flowing before it is motivated either by the force of gravity or suction to flow out of the same nare that it entered the nasal passageway.

Another method of treating bleeding in a nasal passageway is provided to improve patient comfort by enabling the patient to condition themselves to the therapeutic temperatures wherein irrigant at a temperature less than 46 degrees Celsius is motivated to flow into or through a bleeding nasal passageway then the temperature of the irrigant is increased and maintained in the range of 46 degrees Celsius to 52 degrees Celsius.

Patient comfort and hemostasis are achieved when the irrigant flow rate is maintained between 2.5 cc/second and 10 cc/second when the irrigant is at 50 degrees Celsius. Temperatures between 48 degrees Celsius and 50 degrees Celsius are more tolerable and provide adequate therapeutic effect as compared to temperatures above 50 degrees Celsius. The ideal balance of patient comfort, volume of irrigant, and flow rate are temperatures between 48 degrees Celsius and 50 degrees Celsius, 1000 cc liquid, and 3 cc per second to 5 cc per second.

FIG. 1 is a perspective view of a unit for heating and pumping an irrigant for treating bleeding according to certain embodiments of the invention. A lid 1 covers a reservoir 2. The lid 1 may be removable or fixed to the reservoir 2. If fixed in place, the lid 1 may be configured with an element to facilitate filling the reservoir 2 with irrigant. A switch 3 turns the electrical power on or off (labeled in FIG. 1 as "ON" and "OFF). An LCD screen 4 provides information about the status of" the unit such as current temperature, set temperature, fault codes, etc. A power cord 5 includes a receptacle that plugs into an electrical socket to provide electrical power to the unit. An irrigant nozzle 6 is where the heated irrigant exits the unit. The irrigant nozzle 6 has provisions for attaching various therapy delivery devices to enable therapeutic irrigant to flow to a therapy site. An enclosure 7 houses several components of the unit. A down button 8 enables the user to select and/or adjust various features indicated on the screen such as menu options, temperature settings, and irrigant flow rate settings. An up button 9 enables the user to select and/or adjust various features indicated on the screen such as menu options, temperature settings, and irrigant flow rate settings. An insulated wall 10 of the reservoir 2 reduces heat loss from the irrigant to provide a more stable irrigant temperature.

Figure 2:
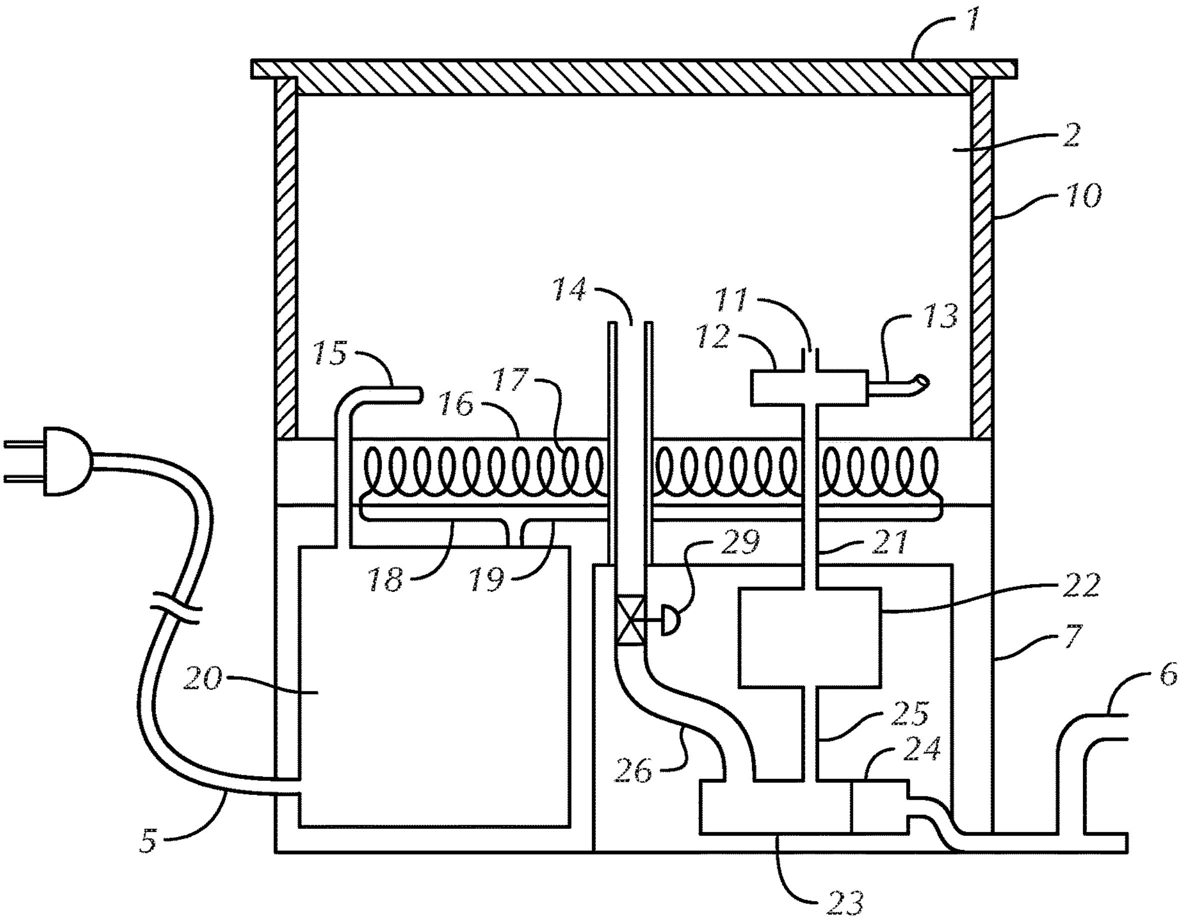
FIG. 2 is a cross-sectional view of an apparatus for heating and pumping an irrigant for treating bleeding according to certain embodiments of the invention.

FIG. 2 is a cross-sectional view of a unit for heating and pumping an irrigant for treating bleeding according to certain embodiments of the invention. A recirculating inlet 11 allows the irrigant from the reservoir 2 to enter a recirculating impeller 12. The recirculating impeller 12 is attached to a motor 22 by a recirculating impeller shaft 21 and motivates water to exit a recirculating impeller nozzle 13 to maintain circulating movement of irrigant in the reservoir 2. A main impeller inlet 14 allows water from the reservoir 2 to enter a main impeller inlet tube 26, which fluidly communicates with a main impeller 23. A temperature sensor 15 senses the temperature of the irrigant in the reservoir 2 and electrically communicates the information to an electronic controller 20, which adjusts the electrical power applied to a heater 17 to control the temperature of the irrigant in the reservoir 2. A reservoir base 16 forms the bottom of the reservoir 2.

The heater 17 may include an electrically resistive heating wire such as nickel chromium wire to increase the temperature of the irrigant in the reservoir 2. These heater wires 18, 19 conduct the electricity from an electrical relay to the heater 17. The electronic controller 20 controls the various functions of the system such as irrigant temperature by adjusting the amount of electrical energy conducted to the heater 17 based on: (i) the temperature information provided by the temperature sensor 15; (ii) the irrigant flow rate exiting the irrigant nozzle 6 by adjusting the speed of the motor 22 based on the information provided by an irrigant flow rate sensor 24; (iii) preventing the irrigant valve 29 from opening until the irrigant is within the therapeutic temperature range, and (iv) providing information for the LCD display 4.

The motor 22 simultaneously spins both the recirculating impeller 12 and the main impeller 23 to motivate irrigant to flow out of the recirculating impeller nozzle 13 and the irrigant nozzle 6. The irrigant flow rate sensor 24 provides irrigant flow rate information to the controller 20 to enable adjustments to speed of the motor 22, which in turn adjusts the irrigant flow rate. A main impeller shaft 25 connects the motor 22 to the main impeller 23. A main impeller inlet tube 26 fluidly connects the reservoir 2 to the main impeller 23. An LED on the outside of the unit illuminates the indicator RED when the unit is on but the irrigant temperature is not in the therapeutic range and the indicator GREEN when the unit is on and the irrigant temperature is in the therapeutic range. A start button on the outside of the unit is actuated by the user to commence the therapy by opening the irrigant valve 29 to enable the flow of irrigant to the main impeller 23, where the irrigant is then motivated to flow out of the nozzle 6 and to the site of therapy.

Figure 3:
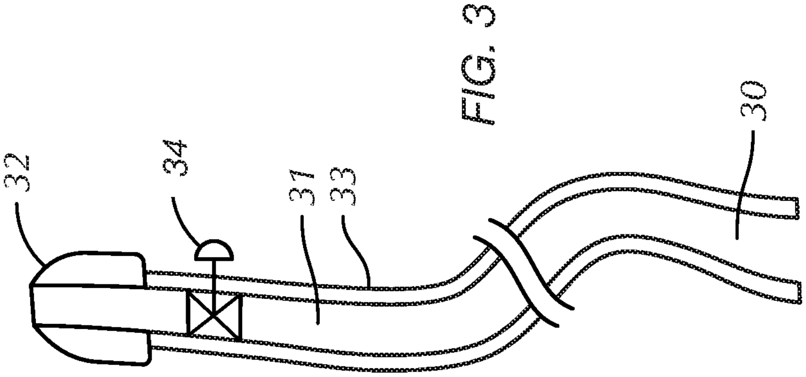
FIG. 3 is a cross-sectional view of an apparatus for supplying an irrigant for treating bleeding according to certain embodiments of the invention.

FIG. 3 is a cross-sectional view of an apparatus supplying irrigant for treating bleeding according to certain embodiments of the invention. A nozzle interface 30 connects to the nozzle 6 to deliver the therapeutic irrigant to a nasal passageway through a nasal therapy tube lumen 31. A nasal interface 32 seals against the nare to enable the therapeutic irrigant to flow into the nasal passageway. A tubing wall 33 is the wall of the nasal therapy tube and defines the nasal therapy tube lumen 31. A tubing valve 34 is actuated by the user to enable the flow of irrigant through the nasal therapy tube lumen 31.

Figure 4:
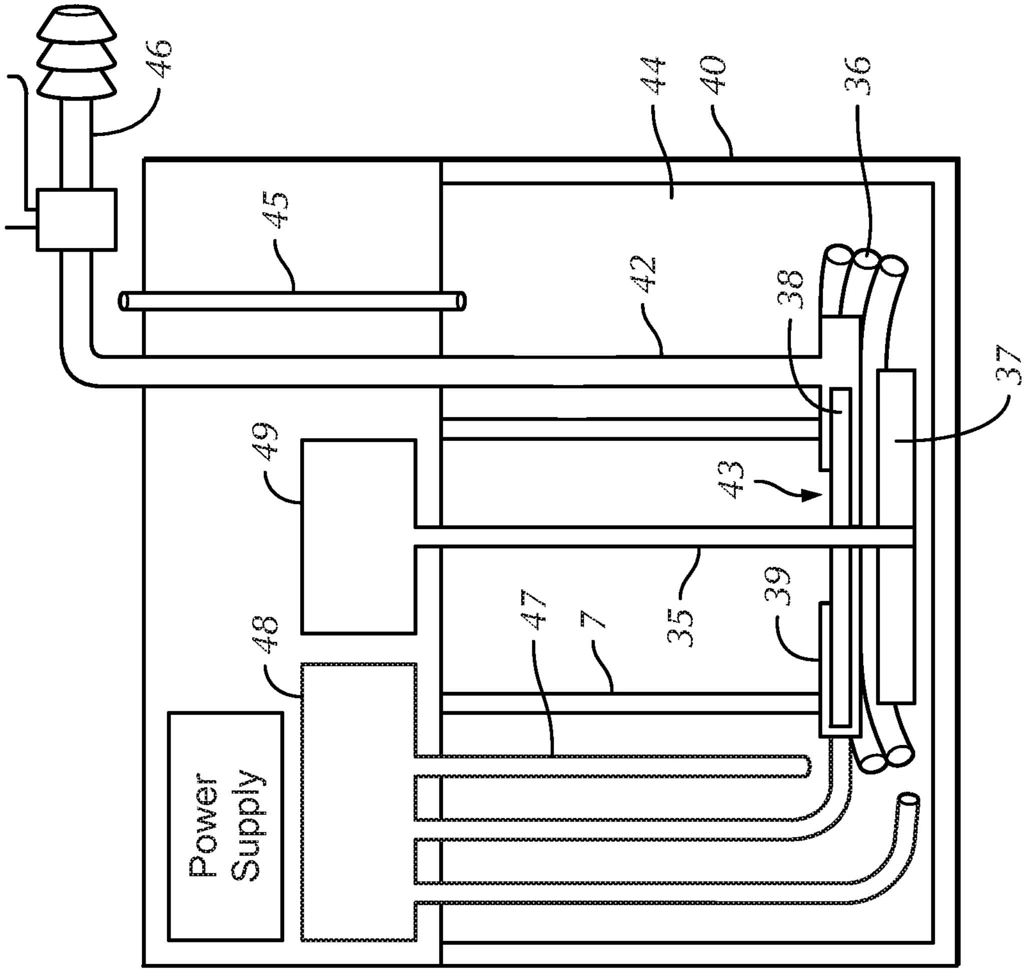
FIG. 4 is a cross-sectional view of another apparatus for heating and pumping an irrigant for treating bleeding according to certain embodiments of the invention.

FIG. 4 is a cross-sectional view of another apparatus for heating and pumping an irrigant for treating bleeding according to certain embodiments of the invention. A recirculating impeller 37 is attached to a motor 22 by a recirculating impeller shaft 35 and motivates water to circulate an irrigant in a reservoir 44. The reservoir 44 includes an insulating wall 40. A main impeller inlet 43 allows water from the reservoir 44 to enter a main impeller housing 39. A temperature sensor 47 senses the temperature of the irrigant in the reservoir 44 and electrically communicates the information to a temperature controller 48, which adjusts the electrical power applied to a heater 36 to control the temperature of the irrigant in the reservoir 44. The heater 36 may include an electrically resistive heating wire such as nickel chromium wire to increase the temperature of the irrigant in the reservoir 44. The motor 49 simultaneously spins both the recirculating impeller 37 and a main impeller 38 to motivate irrigant to flow out of the stopcock 46 via an exit conduit 42. Air can enter the reservoir 44 to take the place of irrigant leaving the reservoir via a vent tube 45. A main impeller shaft 35 connects the motor 49 to the main impeller 38 and the recirculating impeller 37. The flow of irrigant to the therapy site is commenced by opening the stopcock 46 to enable the flow of irrigant as motivated by the main impeller 38 to the site of therapy.

In another embodiment, a device is provided for treating bleeding in the stomach. The device is the irrigant therapy heating and pump device with the effluent receptacle described herein and includes at least one conduit configured to communicate with the stomach. The conduit may be used for the therapeutic irrigant to flow into the stomach. Additionally, the same conduit may be used for the contents of the stomach and the therapeutic irrigant to flow from the stomach and into the effluent receptacle. If a single conduit is used for flow in both directions, a valve is necessary to direct the irrigant from the stomach and into the effluent container and from the reservoir into the stomach. It is understood that the irrigant may include substances to stop bleeding.

Any method of motivating irrigant flow to lavage the stomach may be used in addition to a pump such as the force of gravity or an air pressure differential between the reservoir and effluent container. Additionally, a pump to motivate irrigant into the stomach may be used in concert with a source of vacuum to draw irrigant and irrigant out of the stomach. Furthermore, the pump and vacuum source may be powered in any manner such as using electrical power from batteries or from an alternating current source or via a manual pump.

Another embodiment is similar to that described herein but does not collect the effluent and instead allows it to flow into a separate container, basin, or drain.

A method of treating upper gastrointestinal bleeding is provided wherein a conduit (such as a nasogastric tube) with at least one lumen is positioned to fluidly communicate with a patient's stomach wherein the stomach is lavaged with an irrigant in the temperature range of 46 degrees Celsius to 52 degrees Celsius. A single lumen conduit may be used to both lavage the stomach with irrigant, then let the irrigant reside in the stomach for a period of time before evacuating at least a portion of the irrigant through the single lumen conduit. Alternatively, a dual lumen conduit may be used where one lumen is used for flow into the stomach and the second lumen is used for flow out of the stomach to circulate irrigant through the stomach and control the volume of irrigant in the stomach.

Figure 5:
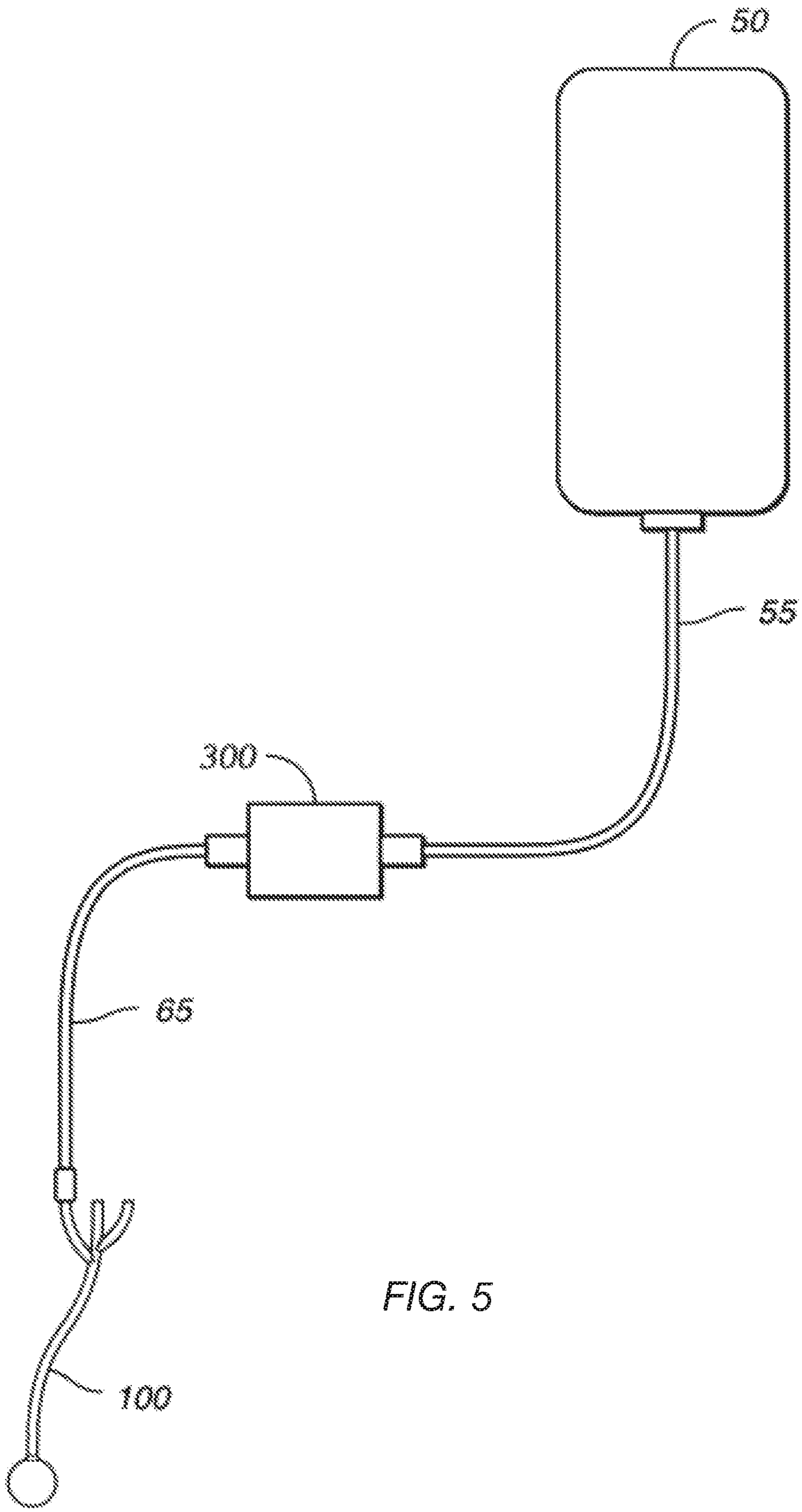
FIG. 5 is a schematic view of a system including an apparatus for heating and pumping an irrigant for treating bleeding according to certain embodiments of the invention.

FIG. 5 is a schematic view of a system including an apparatus for heating and pumping an irrigant for treating bleeding according to certain embodiments of the invention. An irrigant source 50 is connected to a heating apparatus 300 via a source tubing 55. The irrigant source 50 can be any type of container or reservoir for the desired irrigant fluid. In certain embodiments, the irrigant source 50 is a saline hag of the type commonly found in healthcare facilities or any equivalent container or reservoir for saline of other medically suitable fluid. The source tubing 55 is connected to the irrigant source 50 through the convention means of connecting items like saline bags to medical tubing. Similarly, the source tubing 55 is connected to the heating apparatus 300 via a suitable port, valve, lock, or other connection apparatus. The heating apparatus 300 may preferably have a shutoff valve at the connection point with the source tubing 55 to enable easy replacement of disposable elements on the heating apparatus as described in further detail herein.

Referring still to FIG. 5, the heating apparatus 300 is connected to a treatment catheter 100 via a delivery tubing 65, which delivers heated irrigant to the treatment catheter 100 for treating bleeding within a patient. The delivery tubing 65 is connected to the heating apparatus 300 via a suitable port, valve, lock, or other connection apparatus. The heating apparatus 300 may preferably have a shutoff valve at the connection point with the delivery tubing 65 to enable easy replacement of disposable elements on the heating apparatus as described in further detail herein. The delivery tubing 65 is connected to the treatment catheter 100 via a suitable port, valve, lock, or other connection apparatus and may preferably have a shutoff valve at the connection point with the treatment catheter 100 to enable easy exchange of the treatment catheter 100 with another treatment device.

In certain embodiments, the irrigant is motivated to travel from the irrigant source 50 to the heating apparatus 300 via a gravity feed, a pressure differential, a mechanical pumping system, or other similar methods. FIG. 5 depicts the irrigant source 50 as elevated above the heating apparatus 300 such that gravity may be sufficient to provide the desired flow rates of the irrigant. In such an embodiment, adjustable valves on the heating apparatus 300, such as those valves contemplated as being present at the connection points with the supply tubing 55 and the delivery tubing 65, may provide sufficient control over the gravity-fed flow rates. In another embodiment, or as an additional flow rate control mechanism, a pump can be included within the heating apparatus 300 depicted in FIG. 5. In such embodiments, the pump and heater interact in a way similar to that described above.

Figure 6:
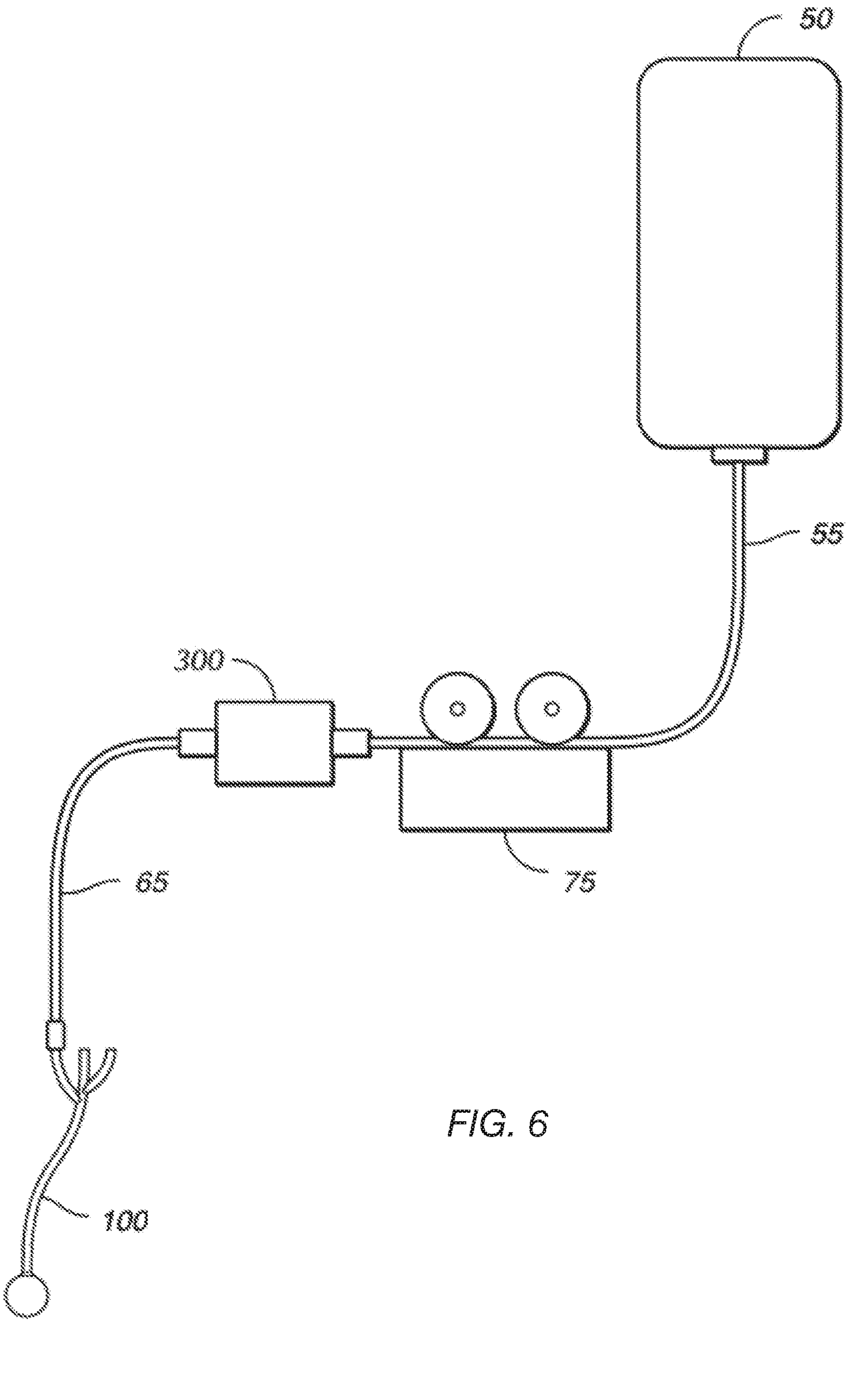
FIG. 6 is a schematic view of another system including an apparatus for heating and pumping an irrigant for treating bleeding according to certain embodiments of the invention.

FIG. 6 is a schematic view of another system including an apparatus for heating and pumping an irrigant for treating bleeding according to certain embodiments of the invention. In this system, the source tubing 55 is connected with a mechanical pump 75 and then the source tubing 55 attached to the heating apparatus 300. This embodiment illustrates that a mechanical pump 75 can be physically separate from the heating apparatus 300. In some embodiments, the mechanical pump 75 may be between the irrigant source 50 and the heating apparatus 300. In other embodiments, the mechanical pump 75 may be between the heating apparatus 300 and the treatment catheter 100.

The embodiments of the systems depicted in FIG. 5 and FIG. 6 and described herein can have control and sensing features consistent with those described above for the embodiments depicted in FIG. 2 and FIG. 4. That is, the heating apparatus 300 and/or any pump associated with the heating apparatus (whether it is a mechanical pump such as that depicted in FIG. 6 or electronically controllable valves at the fluid connection points of the heating apparatus 300) can include an electronic controller to control the various functions of the system. The controller can control an irrigant temperature by adjusting the amount of electrical energy conducted to the heater. The controller can gather temperature information provided by a temperature sensor and irrigant flow rate information from a flow rate sensor positioned at one or more points on the system and can provide such information to a display. The display can include menu options, temperature settings, and irrigant flow rate settings. Other functions disclosed herein can be performed by the controller associated with the heating apparatus 300 and/or any pump associated with the heating apparatus.

Figure 7:
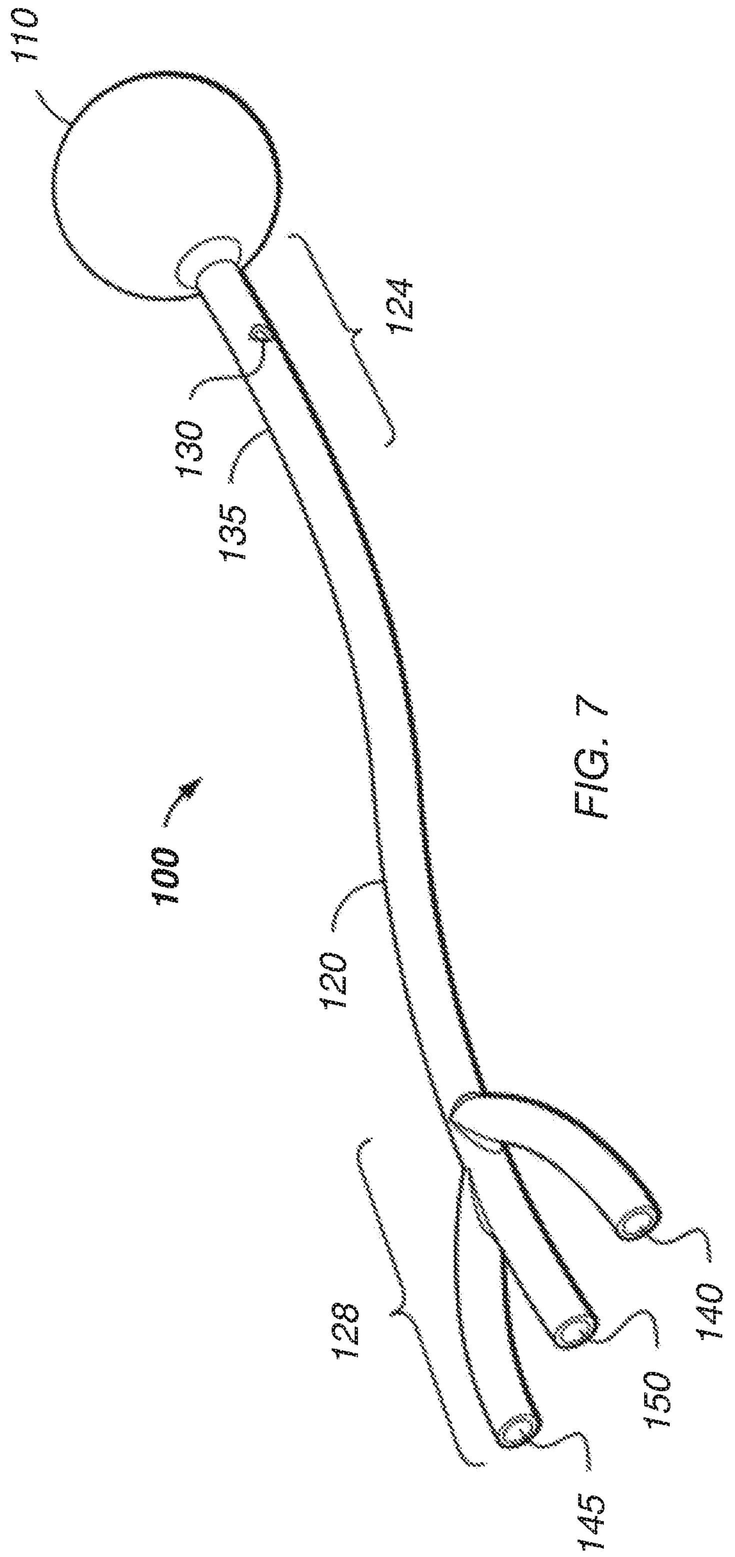
FIG. 7 is a perspective view of an apparatus for supplying an irrigant for treating bleeding according to certain embodiments of the invention.

FIG. 7 is a perspective view of an apparatus for supplying irrigant for treating bleeding according to certain embodiments of the invention. The apparatus of FIG. 7 may be particularly suited for treating bleeding in the urethra and more generally in the urinary tract. A treatment catheter 100 includes an anchoring member 110 attached to a catheter body 120 at a catheter body distal portion 124. The anchoring member 110 is configured to maintain the position of the treatment catheter 100 within a patient's body during treatment and, in some embodiments, to provide a distal fluid barrier such that the heated irrigant does not flow distally beyond the treatment area. FIG. 7 depicts the anchoring member 110 as an inflatable structure that can be inflated via an anchor activation lumen 150. Various inflation methods are available to a user to inflate the anchoring member, such as by passing fluid into the inflatable structure of the anchoring member via a syringe or other similar mechanism. However, anchoring members other than an inflatable structure may be used as long as such anchoring members are configured to hold the treatment catheter at or near the treatment area. For example, the anchoring member could be one or more projecting structures capable of being retracted and projected to engage tissue. And in some embodiments, an anchoring member may not be necessary to hold the treatment catheter at or near the treatment area.

Referring still to FIG. 7, the catheter body distal portion 124 includes a distal outlet 130 and a distal inlet 135. The heated irrigant exits the catheter body 120 at the distal outlet 130 to irrigate the treatment area. The heated irrigant then passes back into the catheter body 120 via the distal inlet 135. The catheter body includes a catheter body proximal portion 128, which in turn includes a proximal inlet 140 and a proximal outlet 145. The proximal inlet 140 is the part of the treatment catheter 100 that receives irrigant from the heater apparatus via a connection with the delivery tubing. The proximal outlet 145 allows for discharge of the irrigant from the treatment catheter 100 to a location where the irrigant can be recirculated or collected. Alternatively, the positions of each inlet and outlet may be reversed.

Figure 8A:
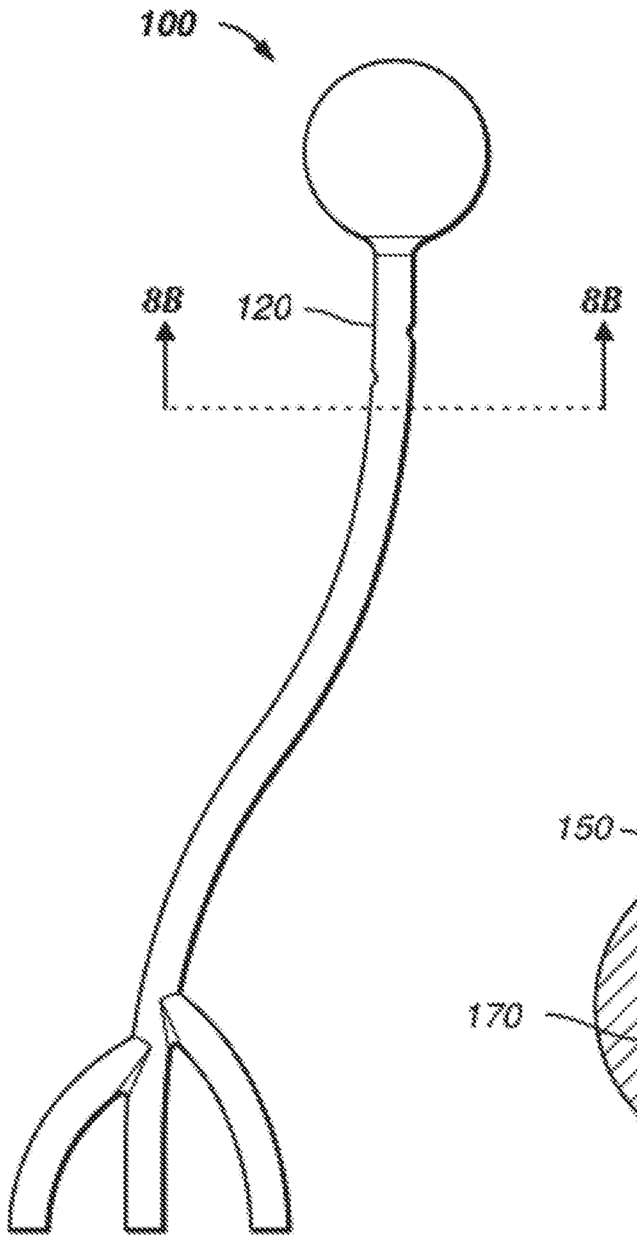
FIG. 8A is a planar view of an apparatus for supplying an irrigant for treating bleeding according to certain embodiments of the invention.
Figure 8B:
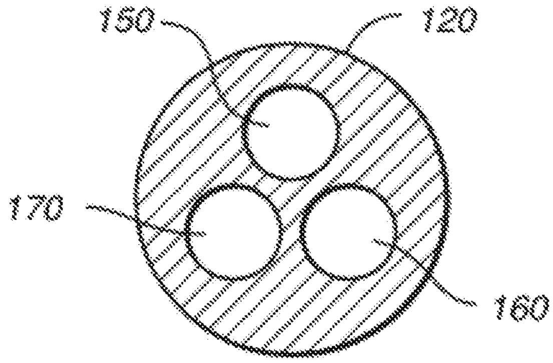
FIG. 8B is a cross-sectional view of the apparatus of FIG. 8A at a certain point along the apparatus according to certain embodiments of the invention.

FIG. 8A is a planar view of an apparatus for supplying an irrigant for treating bleeding according to certain embodiments of the invention and FIG. 8B is a cross-sectional view of the apparatus of FIG. 8A at line 8B. FIG. 8B depicts an arrangement of a supply lumen 160, a drainage lumen 170, and the anchor activation lumen 150 within the catheter body 120. The supply lumen 160 connects the proximal inlet

140 with the distal outlet 130 and is the conduit for the irrigant within the catheter body to the treatment area. The drainage lumen 170 connects the distal inlet 135 with the proximal outlet 140 and is the conduit for the irrigant within the catheter body from the treatment area. The anchor activation lumen 150 is the conduit for the activation mechanism for the anchoring member 110, and in some embodiments that mechanism is a fluid that inflates a structure.

Figure 9A:
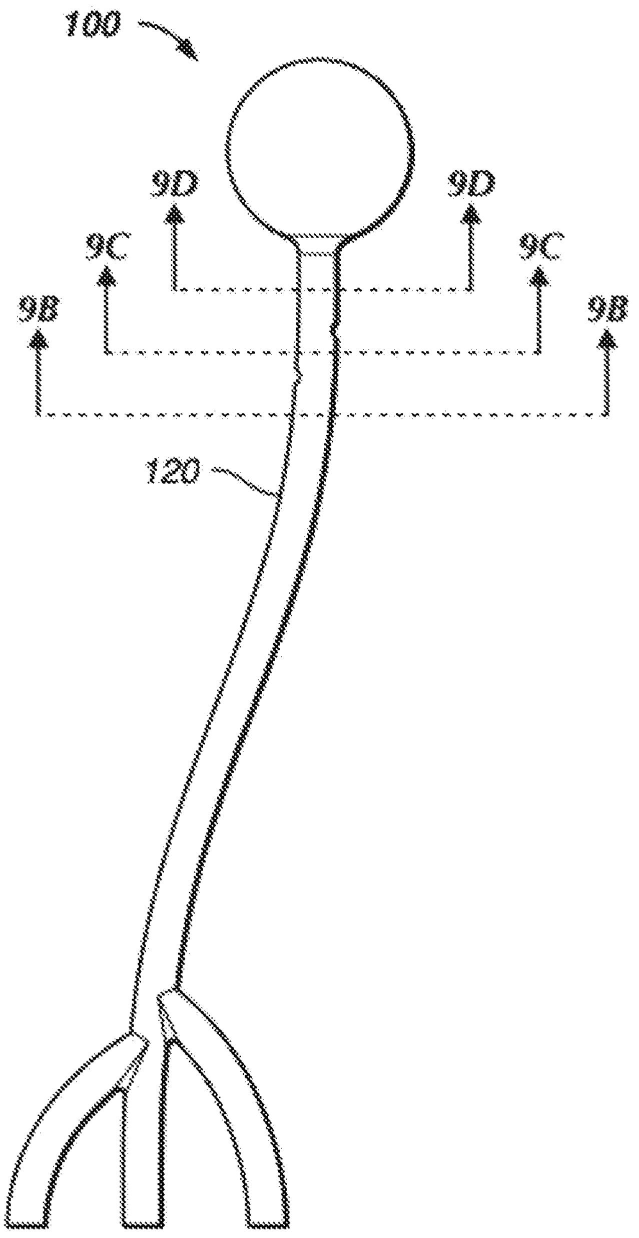
FIG. 9A is a planar view of another apparatus for supplying an irrigant for treating bleeding according to certain embodiments of the invention.
Figure 9B:
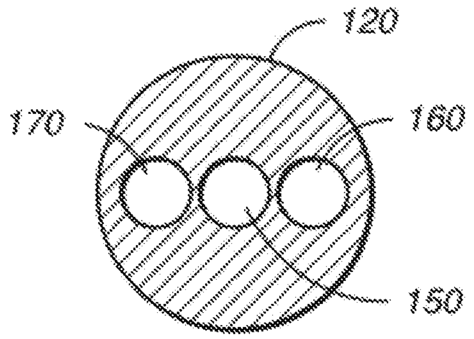
FIG. 9B is a cross-sectional view of the apparatus of FIG. 9A at ace a t along the apparatus according to certain embodiments of the invention.
Figure 9C:
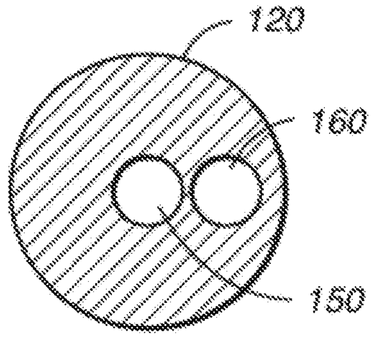
FIG. 9C is a cross-sectional view of the apparatus of FIG. 9A at a certain point along the apparatus according to certain embodiments of the invention.
Figure 9D:
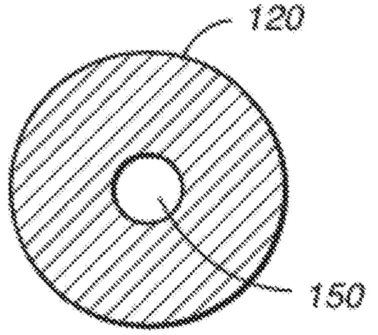
FIG. 9D is a cross-sectional view of the apparatus of FIG. 9A at a certain point along the apparatus according to certain embodiments of the invention.

FIG. 9A is a planar view of another apparatus for supplying an irrigant for treating bleeding according to certain embodiments of the invention. FIG. 9B is a cross-sectional view of the apparatus of FIG. 9A at line 9B, FIG. 9C is a cross-sectional view of the apparatus of FIG. 9A at line 9C, and FIG. 9D is a cross-sectional view of the apparatus of FIG. 9A at line 9D. FIGS. 9B-9D illustrate a different arrangement of the supply lumen 160, the drainage lumen 170, and the anchor activation lumen 150 within the catheter body 120. Other arrangements are within the scope of this disclosure.

The treatment catheters depicted in the FIG. 8A and FIG. 9A, and other treatment catheters configured to function as heated irrigant treatment catheters according to the descriptions presented herein, may include sensors configured to provide relevant information to the controller unit on the heating apparatus and/or pump. For example, the treatment catheter may be equipped with one or more temperature sensors for detecting the temperature of the irrigant at a variety of locations, such as: (i) at or near the proximal inlet; (ii) at or near the distal outlet; (iii) at or near the anchoring member; (iv) at or near the distal inlet; and (v) at or near the distal outlet. Similarly, the treatment catheter may be equipped with one or more flow sensors at a variety of locations, including the five locations listed for the temperature sensors. The information gathered by the temperature and/or flow sensors, and any other sensors present on the treatment catheter, can be in communication (wired or wirelessly) with the controller unit.

Figure 10:
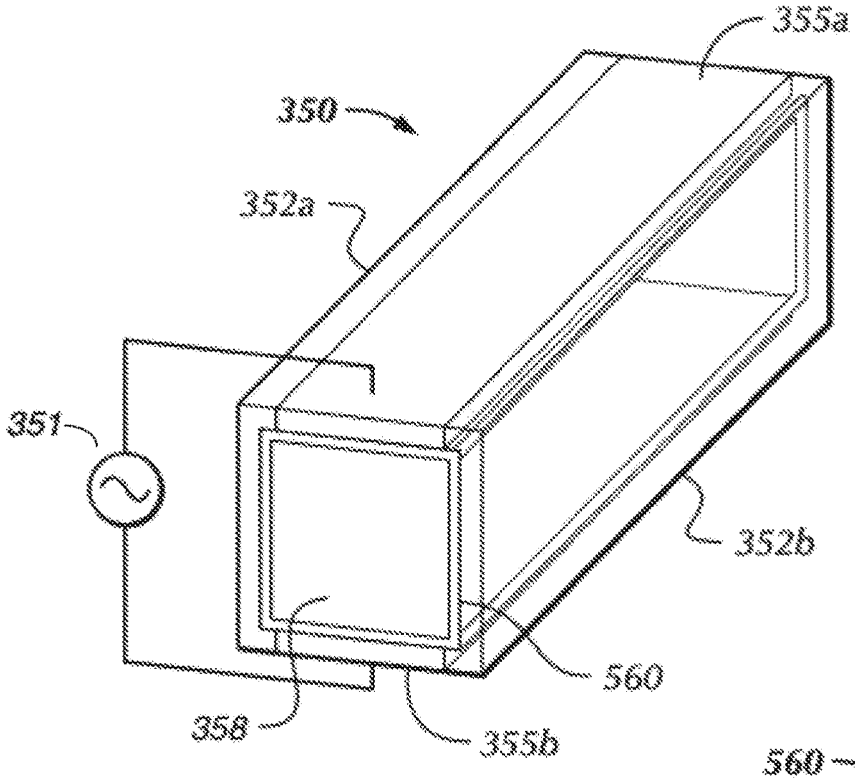
FIG. 10 is a perspective view of a heating element of an apparatus for heating an irrigant for treating bleeding according to certain embodiments of the invention.

FIG. 10 is a perspective view of a heating element 350 of an apparatus for heating an irrigant for treating bleeding according to certain embodiments of the invention. As shown in FIG. 10, the heating element 350 is connected to an electrical power source 351 having electrical connections to a first electrode 355*a* and to a second electrode 355*b*. The electrodes 355*a* and 355*b* may be formed from an electrically conductive material, such as copper, or another electrically conducive metal, and may be spaced apart from one another by an area that includes a hollow cavity forming and at least partially enclosing a fluid passageway 358. Fluid passageway 358 may be configured to receive a flow of irrigant, such as saline, or another fluid intended to be introduced into a patient, such as a human or an animal, after passing through the fluid passageway and being heated to a desired temperature during the time the fluid is transported through the passageway. The heating of the fluid flow is accomplished by the application of electrical energy provided to the electrodes 355*a*, 355*b* from the electrical power source 351. The electrodes 355*a* and 355*b* may be referred to as one example of a set of electrodes. Electrical energy provided to the electrodes 355*a*, 355*b* is operable to produce an electromagnetic field in the area between the electrodes, which includes the fluid passageway 358, and to generate non-contact RF heating of a fluid that is flowing through or that is contained within the fluid passageway, without having any direct physical contact with or being immersed into the fluid that is flowing through the fluid passageway.

In the heating element 350, a liner 560 at least partially surrounds the fluid passageway 358, and isolates the fluid passageway from the electrodes 355*a*, 355*b* so that the fluid passing through the fluid passageway 358 is not brought into contact with the electrodes. In some embodiments, the liner 560 functions as a dielectric barrier and may be formed from an insulating material, such as but not limited to a plastic material such as polyimide. In various embodiments, the liner 560 may be part of the heating element body, and may be configured as a disposable sterile insert, that is inserted within and extends through the fluid passageway 358 to provide a sterile environment for the fluid to flow through while flowing through the fluid passageway. In some embodiments, the liner 560 is part of the sterile environment used in contact with and to provide a conduit for the flow of fluid through the fluid passageway 358, and is removable and disposable after use in a fluid warming procedure utilizing heating element 350. A heating element body may be configured to hold the electrodes 355*a*, 355*b* in a position spaced apart from one another and proximate to the fluid passageway 358, such as by being held by a first side plate 352*a* and a second side plate 352*b*. Electrode 355*a* and/or electrode 355*b* may be partially or wholly embedded within a body in some embodiments in order to maintain the proper positioning of the electrodes relative to each other and to the liner 560 and the fluid passageway 358.

As further described below, the heating element 350 may be configured to provide and control electrical energy that is output from the electrical power source 351 and provided to the electrodes 355*a*, 355*b*, in order to provide a controlled heating of the fluid flowing through the fluid passageway 358, such as a fluid intended for introduction into a patient, while the fluid flows through or is present within the fluid passageway. The heating element 350 may be further configured to warm the flow of fluid through the fluid passageway 358 while maintaining a sterile environment with respect to any of the passageways and fluid conduits that conic into direct contact with the fluid being heated subsequent to the introduction to the patient.

In some embodiments, heat energy is transferred to the irrigant via conduction, convection, microwave energy, or other equivalent forms of heating a liquid. In some embodiments, the preferred method of heating the irrigant is via non-contact radio-frequency heating.

Embodiments of the non-contact radio-frequency heating may be performed using frequencies in a range of 10 kHz to 30 MHz, or as high as 100 MHz, or as high as 300 GHz, which may allow a volume of liquid to be heated faster with a lower surface area to volume ratio as the energy is transferred into the liquid more uniformly. The energy may also be transferred into the liquid through a non-conductive surface to eliminate the risk of forming steam and/or bubbles due to "hot spots" generally accompanied with rapid heating using conductive methods. The end result is similar to microwave heating of a liquid except higher electrical to thermal efficiencies can be realized. Using a resonant inverter at megahertz frequencies also may provide very fast response time and fine control over the heating system. Strategies for passive/natural power factor correction may be incorporated that limit or eliminate the need for an active power factor correction stage common in more conventional switching regulators. In various embodiments, the control circuitry of the control unit may provide output signals to control a device, such as fluid pump, wherein the flow rate of the liquid is adjusted so as to maintain the monitored temperature at, or within a band around, a constant value.

In various embodiments, the passageway for the flow of fluid to be heated includes a flexible passageway. In various embodiments, the fluid to be heated is an ionic liquid. In various embodiments, the fluid to be heated is saline, and is physiological saline. In various embodiments, wherein the temperature of the fluid being heated is to be maintained within a temperature range of between 49° C. and 51° C., inclusive. In various embodiments, the fluid exiting the conduit conveying the heated fluid from the non-contact radio-frequency heating element is configured for conveying heat to a liquid and delivering said liquid at a temperature elevated above that of the human body into an external body orifice, such as but not limited to a urinary meatus of a patient. Various embodiments further include a catheter extending through the urethra of a patient for receipt within the bladder and configured to convey a fluid heated by a non-contact radio-frequency heating unit to the bladder of a patient.

In various embodiments, the control unit includes a resonant inverter, such as but not limited to a Class E resonant inverter. In various embodiments, the Class E resonant inverter further comprises a wide-bandgap transistor, and/or wherein the signal driving the gate of the transistor comprising the Class E resonant inverter is supplied by the microcontroller. In various embodiments, the supply to the Class E resonant inverter is the unfiltered rectified line voltage. In various embodiments, the input voltage of the resonant electrical waveform generator is configured to vary in time at the fundamental of the line frequency (50 Hz or 60 Hz), and as a result the current drawn by the electrical waveform generator scales with voltage. If the voltage at the input of the electrical waveform generator is allowed to drop nearly to zero in sync with the rectified line, the electrical waveform generator itself may present approximately a resistive load to the line, and therefore nearly unity power factor can be achieved without any active or passive filtering elements.

In various embodiments, one or more of the temperature sensors configured to provide an output signal to the control unit may be read by the control circuitry during an OFF cycle of the modulation of the electrical output waveform(s) being provided to the electrode output terminal of the control unit. Temperature (and other) measurements may be susceptible to noise from switching power converters. Incorporation of temperature sensor(s) that can be read during the off-cycle modulation such that no switching noise is present, greatly improving the accuracy of the temperature reading. In various embodiments, one or more of the temperature sensors configured to provide an output signal to the control unit may be read during a minimum voltage level of the rectified line voltage. The gating of the resonant electrical waveform generator is disabled at the minimum rectified line voltage at the point of approximately zero power such that the temperature reading and off period do not adversely affect the power factor characteristics of the system.

In various embodiments, the ON and OFF switching cycles and the modulation periods may be synchronized with the line voltage or other electrical power input provided to the control unit. In various embodiments, the principal AC frequency, or the duty cycle of the transistor gate drive signal, are adjusted so as to optimize the heating efficiency, delivered power, or the power factor of the apparatus. As input voltage to the resonant electrical waveform generator varies with the rectified line voltage or otherwise, the optimal switching frequency and/or duty cycle may be affected, leading to reduced efficiency and/or power factor. Varying frequency and/or duty cycle can lead to optimal efficiency and power factor for a given instantaneous input voltage or load impedance. Frequency and/or duty cycle may also be used to control power delivered to the load by deliberately tuning/detuning the impedance seen by the electrical waveform generator.

In various embodiments the control unit in conjunction with a non-contact radio-frequency heating element may utilize high voltage DC pulses to transfer electrical energy into a liquid. The process of pulse electric field sterilization (PEF) is a method of applying high voltage DC pulses (could be bipolar DC voltages) to a liquid in order to destroy the cell walls of any bacteria that may be present within the liquid. In addition to sterilizing the liquid, the temperature of the liquid also increases moderately. PEF can be used to both sterilize and heat the liquid in real-time. The DC pulses can be on the order of 1 microsecond or greater in length. Generally, electric field strengths of 800 V/mm or higher are desired to achieve significant bacteria reduction in a liquid. The electrode strategy is similar to the AC method but in various embodiments may have exposed electrodes in contact with the liquid, such as metal electrodes.

Figure 11A:
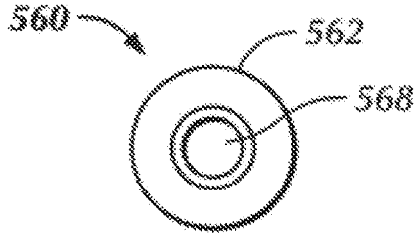
FIG. 11A is an end view of a liner for a heating element of an apparatus for heating an irrigant for treating bleeding according to certain embodiments of the invention.
Figure 11B:
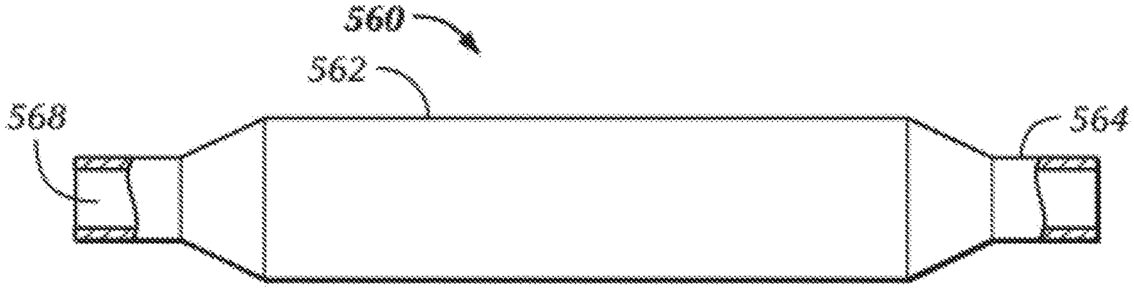
FIG. 11B is a side view of a liner for a heating element of an apparatus for heating an irrigant for treating bleeding according to certain embodiments of the invention.

FIG. 11A is an end view and FIG. 11B is a side view of a liner 560 for a heating element of an apparatus for heating an irrigant for treating bleeding according to certain embodiments of the invention. In general, it is preferable that the fluid irrigant passageway 358 be physically separated from the irrigant flowing through the fluid irrigant passageway 358. The separation is desirable to maintain the sterility and/or biocompatibility of the irrigant as it flows through the fluid irrigant passageway 358. If the liner 560 is made from a biocompatible material, then the liner can be periodically replaced, thereby maintaining the operational integrity of the heating element and the sterility and/or biocompatibility of the irrigant.

FIGS. 11A and 11B illustrate that the liner 560 includes a liner cavity 568 through which the irrigant can flow. The liner 560 has an outer surface 562 that is placed in contact with the inside of the fluid irrigant passageway 358 of the heating element 350 and a connection surface 564 that facilitates connection of the liner 560 with the supply tubing on one end and the delivery tubing on the other end. FIGS. 11A and 11B depict a liner 560 with a round cross section, and FIG. 10 depicts a liner 560 with a square cross section. These shapes and other cross sections can be used. Generally, there should be intimate contact between the outer surface 562 of the liner 560 and the inside of the fluid irrigant passageway 358 of the heating element 350. Such contact ensures efficient transfer of heat energy to the irrigant within the liner 560.

In some embodiments, the liner 560 can be replaced each time an irrigant source is connected to the heating apparatus. For example, in an embodiment in which the irrigant source is a saline bag, multiple saline bags may be required for the bleeding treatment. If so, each time the saline bag is disconnected from the heating apparatus (and/or the pump), a new liner 560 can be inserted into the heating element. In another example, an additional therapeutic agent may be added to a first irrigant source and that agent may not be desired to be added to the second irrigant source. In this example, placing a new liner into the heating element prevents residue of the therapeutic agent from being present in the irrigant supplied by the second irrigant source.

There are several advantages to the in-line heating apparatus disclosed herein. The heating apparatus is able to provide quick heating of a volume of irrigant as that irrigant flows through the heating element. Using feedback from sensors, the controller unit precisely controls the temperature and the flow rate of the irrigant through the heating element and into the treatment catheter. The replaceable liner allows for the use of readily available irrigant sources, such as saline bags, and allows for rapid exchange of those irrigant sources during a single treatment session. The replaceable liner allows the heating apparatus to be used with multiple patients without requiring sterilization of the heating element in between patients.

An in-line heating apparatus as disclosed herein may also be used in embodiments in which the irrigant fluid is used to maintain a structure to therapeutic temperature at the treatment site. For example, the treatment catheter may include a structure that is configured to substantially conform to the tissue at the treatment site. Such a conforming structure can include, for example, a balloon, expandable arms, or combinations thereof.

The conforming structure can be filled with the irrigant fluid to bring the conforming structure to a therapeutic temperature, to maintain the conforming structure at a therapeutic temperature, or both. In some embodiments, the conforming structure could be brought to a temperature at or near the therapeutic temperature prior to the treatment catheter being inserted into the patient.

The conforming structure can also be filled, inflated, expanded, or otherwise made to conform to the body cavity using the irrigant fluid. In an embodiment in which the conforming structure includes a balloon, the balloon is connected to a supply lumen to fill the balloon with heated irrigant fluid and a drainage lumen to drain the balloon of the irrigant fluid after the irrigant fluid has transferred heat to the body cavity via the balloon. The irrigant fluid may be circulated within the balloon to maintain the balloon within the therapeutic temperature range, such as in the range of 46 degrees Celsius to 52 degrees Celsius.

The balloon may have a soft pliable wall made from a non-elastomeric polymeric material. The non-elastomeric balloon can be filled with fluid at a low pressure, thereby conforming to the anatomy and applying the warmth from the balloon evenly to the target tissue.

Figure 12:
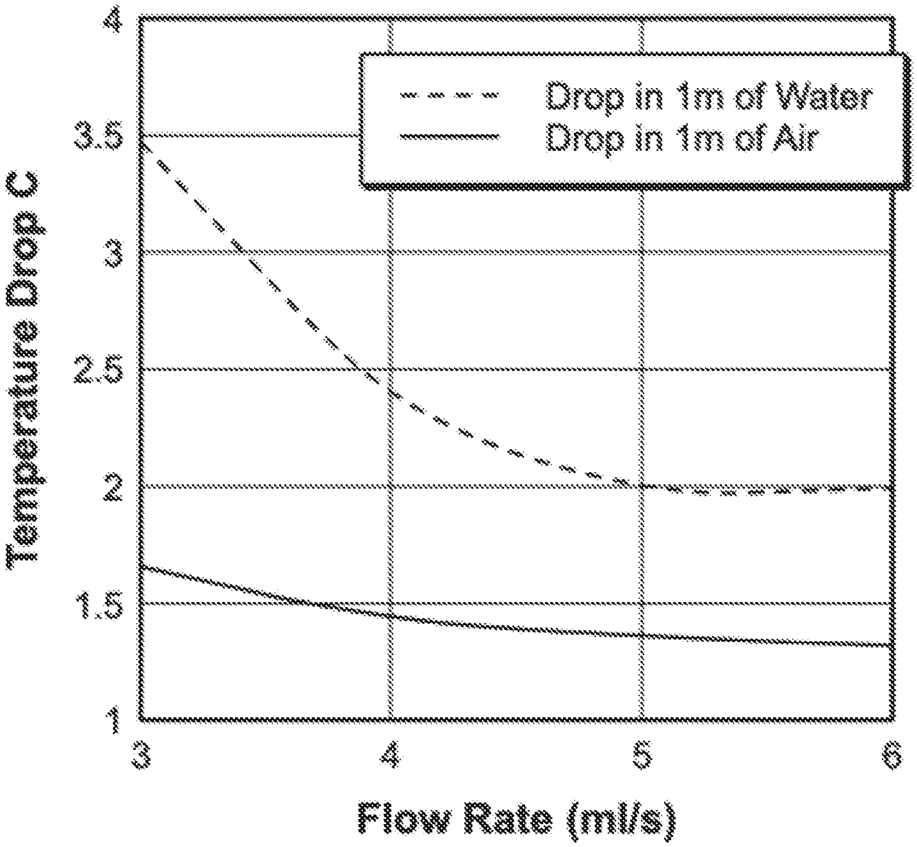
FIG. 12 illustrates temperature data collected in different environmental conditions according to an embodiment of the invention.

FIG. 12 illustrates temperature data collected in different environmental conditions according to an embodiment of the invention, A length of medical grade tubing having has an inner diameter of ⅛" (3.17 mm) and wall thickness of 1/64" (0.4 mm) was connected to heated irrigant (48-52 degrees Celsius). The irrigant was motivated through the tubing at flow rates ranging from 3 cc/s to 6 cc/s. The temperature drop across 1 meter of tubing was recorded via temperature sensors. The solid line on the graph in FIG. 12 shows the temperature drop in degrees Celsius for a meter of tubing held in air with ambient temperature of 2.5 degrees Celsius. The dashed line on the graph in FIG. 12 shows the temperature drop in degrees Celsius for a meter of tubing submerged in water maintained at a temperature of 37 degrees Celsius.

As disclosed herein, 48-52 degrees Celsius is a preferred temperature range for the treatment of bleeding with a heated irrigant. The results of FIG. 12 demonstrate that, at the flow rates identified as therapeutically preferable, it is possible for a heated irrigant to remain within the therapeutic temperature window over transport lengths much greater than those anticipated for actual use. Further, with the presence of temperature sensors providing feedback to the controller unit, it is possible for the heating and pumping apparatus disclosed herein to account for temperature drops experienced in a system, including by heating the irrigant beyond the therapeutic temperature in the heating element and allowing the irrigant to reach the therapeutic temperate via exposure to ambient air temperature or to body temperature.

Figure 13:
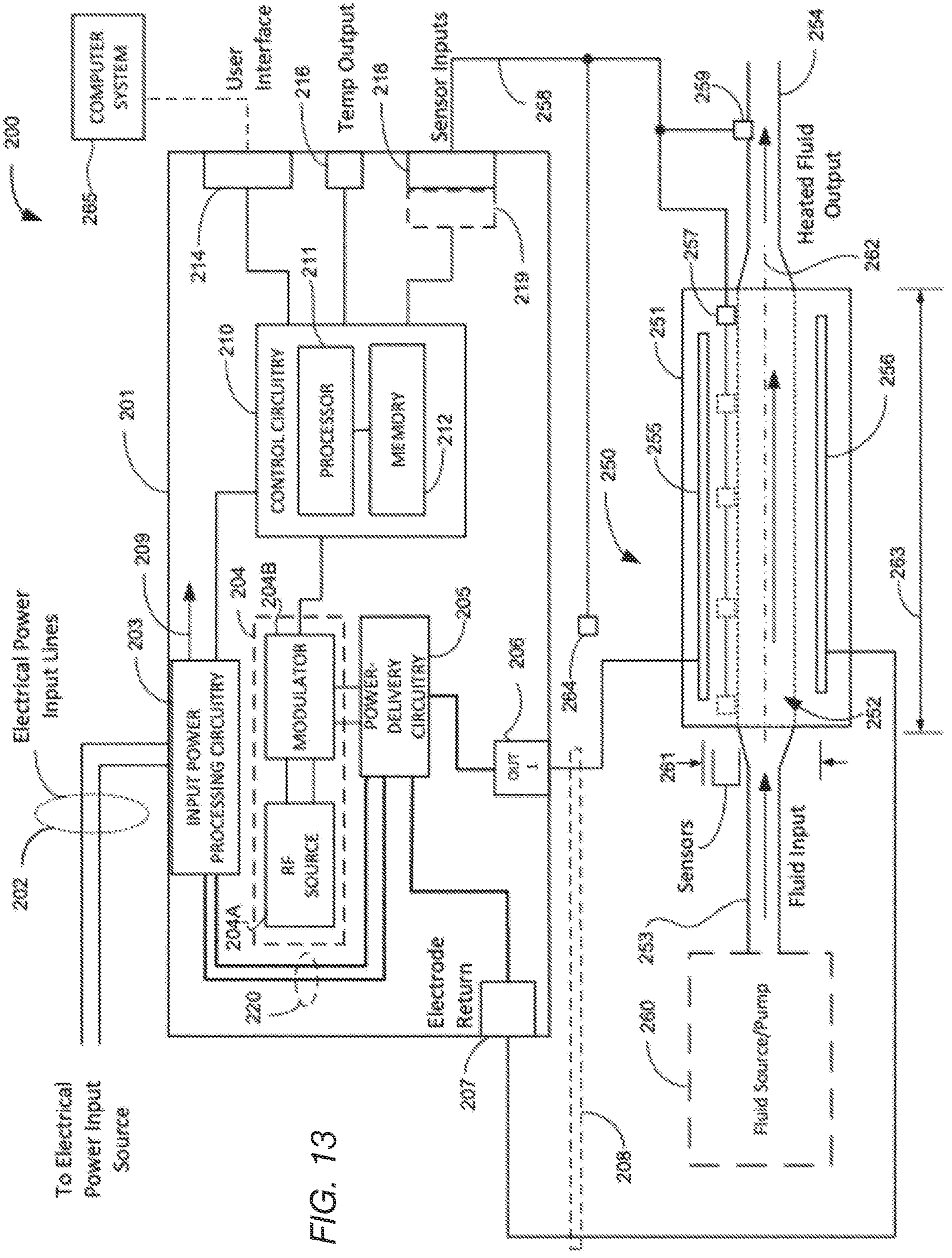
FIG. 13 illustrates a schematic block diagram of a non-contact radio-frequency heating system according to at least one embodiment.

FIG. 13 illustrates a schematic block diagram of a fluid non-contact radio-frequency heating system 200 (hereinafter "system 200") according to at least one embodiment. As shown in FIG. 13, system 200 includes a non-contact RF heating element 250 (hereinafter "element 250") electrically coupled to a non-contact RF heating control unit 201 (hereinafter "control unit 201"). System 200 is configured to provide a controlled level of non-contact RF heating to a flow of fluid passing through element 250 by non-contact RF heating of the fluid flow using electrical energy provided and controlled by control unit 201 and applied to one or more sets of electrodes included in element 250, as further described below.

Element 250 includes a heating element body 251 (hereinafter "body 251") having a first end coupled to a fluid input conduit 253 and a second end that is opposite the first end, the second end coupled to a fluid output conduit 254. A hollow passageway 252 extends from the first end to the second end of the body 251, forming a fluid passageway to transport a flow of fluid entering the first end of body 251 as provided by the fluid input conduit 253 to the second end of the body and to the outlet provided by fluid output conduit 254. Element 250 further includes one or more sets of electrodes positioned within body 251, the electrodes positioned proximate to passageway 252, and sealed from passageway 252, for example by a portion of the body 251, so that the electrodes will not come into contact with the fluid flowing through the passageway. Embodiments of passageway 252 are not limited to being formed as a single straight passageway, and in various embodiments may include a set of parallel passageways, or a single passageway that winds along, for example in a serpentine path or other non-linear path, through the body 251 of element 250.

As illustrated in FIG. 13, element 250 includes a first electrode 255 embedded within body 251 and positioned above passageway 252, and a second electrode, return electrode 256, also embedded within body 251 and positioned below passageway 252 and on the opposite side of the passageway with respect to the position of first electrode 255. Electrode 255 and return electrode 256 have respective surfaces facing the passageway 252 that that are spaced apart from one another by a distance 261. Distance 261 is not limited to a particular distance or range of distances, and in various embodiments includes a distance value in a range of 1 to 10 millimeters, inclusive. Electrode 255 and return electrode 256 in various embodiments are flat planar structures that extend parallel to each other and extend along some length of a longitudinal axis 262 of element 250. However, the configurations of electrode 255 and return electrode 256 are not limited to being shaped as flat planar structures, and may be formed into other shapes, such as but not limited to curved arch-shaped structures that extend radially around at least some portion of longitudinal axis 262 at some radial distance away from the longitudinal axis and extending along at least some portion of the longitudinal axis while remaining physically separated and electrically isolated from one another. Other arrangements for electrode 255 and return electrode 256 are possible and are contemplated for use in system 200. Further, as illustrated in FIG. 13 element 250 has a horizontal orientation along longitudinal axis 262. However, the orientation of a longitudinal axis, and thus the orientation of passageway 252 and/or a plurality of passageways included in an element such as element 250, is not limited to any particular orientation. The orientation of element 250 is not limited to a horizontal orientation while the element is coupled to a control unit and is being used in a RF heating application. In various embodiments, the orientation of the RF heating element may include any orientation, including horizontal orientations, vertical orientations, or any angular orientation between a horizontal and vertical orientation.

Electrical energy provided by control unit 201 to electrode 255 and return electrode 256 may establish an electromagnetic field in an area between the electrodes, which is thus imposed onto a fluid included within passageway 252. The field established between the electrodes may then induce non-contact RF heating of the fluid included in the passageway. By controlling the amount and format to the electrical energy provided to electrode 255 and return electrode 256, control unit 201 may be configured to controllably heat a flow of fluid passing through passageway 252 of element 250. In various embodiments, the fluid to be heated is saline, or a saline solution, which is being provided as a non-limiting example of a fluid that may be introduced into a patient after passing through element 250 and being heated to a desired temperature before being introduced into the patient. In addition, because the saline solution is being provided to the patient and in a medical setting, it is important that the heating of the saline be accomplished without contamination of the saline as part of the heating process. As shown in FIG. 13, because electrode 255 and return electrode 256 are not in contact with the flow of fluid through passageway 252, but instead are configured to provide non-contact RF heating to heat the flow of saline through element 250, system 200 provides a system and method for heating the fluid while maintaining a sterile environment with respect to any of the fluid passageway(s) that might come into contact with the fluid.

In various embodiments, element 250 of system 200 is configured to couple to a fluid source 260, wherein fluid source 260 may include a pump or other mechanism to produce a flow of fluid, such as a flow of saline, to fluid input conduit 253. Fluid input conduit 253 is coupled to the first end of body 251, and is in fluid communication with passageway 252. A flow of fluid, such as saline provided by fluid source 260, may flow through passageway 252 and between electrode 255 and return electrode 256, and exit body 251 through fluid output conduit 254. As the fluid flows through passageway 252, electrical energy under the control of control unit 201 may be provided to electrode 255 and return electrode 256 and produce non-contact RF heating of the fluid within passageway 252. One or more sensors, such as temperature sensor 257, may be positioned proximate to passageway 252, and may be configured to sense the temperature of the flow of fluid as the fluid passes through and exits passageway 252. The sensor(s) generate one or more sensor output signals that are indicative of the sensed temperature of the fluid passing through and/or exiting passageway 252, and provide the output simians) to a sensor input 218 of control unit 201, for example though sensor input lines 258. In some embodiments, sensor input 218 may include or be coupled to a multiplexer 219 configured to multiplex a plurality of input signals from multiple sensors into control circuitry 210, for example using some predefined sampling rate. Control unit 201 may be configured to receive and process the sensor input signal(s)) related to temperature of the fluid, and to further control the output of electrical energy being provided to electrode 255 and return electrode 256 by controlling the electrical output being provided to electrode output terminal 206 and electrode return terminal 207 of the control unit.

In addition to temperature sensing, one or more other types of sensors, such as one or more flow sensors illustratively represented by sensor 259, and one or more ambient temperature sensors illustratively represented by sensor 264, may be included in system 200 to provide additional feedback to control unit 201. In various embodiments, flow sensor 259 is configured to determine a flow rate or a flow volume passing by the sensor, and provide an output signal to control unit 201 indicative of the flow rate or the volume of flow passing by the sensor. This flow rate/flow volume information may be received by control unit 201, and further incorporated into the control of the electrical energy being provided by the control unit to element 250 in order to maintain the temperature control of the flow of fluid passing through element 250 in a desired manner.

In various embodiments, ambient temperature sensor 264 is configured to determine an ambient temperature in one or more areas outside element 250, such as an ambient temperature of the area where the fluid source 260 is located, and/or an ambient temperature in the area where the fluid output conduit 254 passes between the element 250 and the point where the fluid is introduced into a patient. Ambient temperature sensor 264 may be configured to generate and to provide an output signal to control unit 201 indicative of the ambient temperature in one or more areas located outside of element 250. This ambient temperature information may be received by control unit 201, and further incorporated into the control of the electrical energy being provided by the control unit to element 250 to maintain the temperature control of the flow fluid passing through element 250 in a desired manner.

As shown in FIG. 13, control unit 201 includes an input power processing circuitry 203, an electrical waveform generator 204 including a radio-frequency source 204A and a modulator 204B, a power-delivery circuitry 205, and control circuitry 210. Embodiments of control unit 201 may include less or more components, and may include components arranged and coupled in a manner that is different from or varies in some degree or manner from the embodiment shown for system 200 and control unit 201. Variations of the number, types, and arrangements of these components are contemplated by the embodiments of non-contact RF heating control units as described throughout this disclosure, and any equivalents thereof.

As illustrated for system 200, input power processing circuitry 203 is coupled to at least one electrical power input source (not specifically shown in FIG. 13) through electrical power input lines 202. The electrical power input that may be provided to control unit 201 is not limited to any particular type or configuration of electrical power input. In various embodiments, the electrical power input may be a standard electrical power configuration that is provided by a private or government agency in a region where system 200 is being operated. For example, the electrical power input source may be a standardized alternating current (AC) 120 volt/60 hertz line voltage typical of electrical power provided in the United States. In other embodiments, the electrical power input may be a direct current (DC) input supply, for example from a battery or from an electrical power supply. In various embodiments, multiple power sources may be coupled to electrical power input lines 202. For example, lines 202 may be coupled to a conventional AC power source as the main power source, but also coupled to a backup power supply, such as a battery-operated supply or a generator, which is configured to provide electrical power to lines 202 in the event of an electrical power failure of the main power source.

Regardless of the power input configuration, input power processing circuitry 203 may be configured to perform conditioning of the incoming electrical power to provide electrical power that is coupled to the electrical components and devices included in control unit 201, including the electrical waveform generator 204, control circuitry 210, and power-delivery circuitry 205. For the sake of clarity and simplicity, actual lines showing the specific power connections between the electrical components and devices of control unit 201 and the input power processing circuitry 203 may not be illustrated in FIG. 13 but are illustratively represented by arrow 209 extending from the block representing input power processing circuitry 203. Power conditioning provided by input power processing circuitry 203 may include rectification, such as half-wave or full-wave rectification, of an incoming AC electrical power. In various embodiments, power conditioning provided by input power processing circuitry 203 may include filtering, such as low pass, bandpass, or high pass filtering of the power being provided to the electrical components and devices included in control unit 201. In various embodiments, power conditioning provided by input power processing circuitry 203 may include changing a voltage level, a peak voltage level, or a peak-to-peak voltage level of the incoming electrical power relative to the power being provided by the input power processing circuitry to the electrical components and devices included in control unit 201. In various embodiments, power conditioning provided by input power processing circuitry 203 may include making power factor corrections and/or phase adjustments to the incoming electrical power relative to the power being provided by the input power processing circuitry to the electrical components and devices included in control unit 201.

In various embodiments, all or various combinations of these power conditioning processes may be performed by input power processing circuitry 203 on the power being provided by the input power processing circuitry to the electrical components and devices included in control unit 201. In one embodiment, the electrical power input provided to input power processing circuitry includes 120 VAC 60 Hz electrical power, and the output power provided by the input power processing circuitry 203 to the power-delivery circuitry 205 includes a rectified waveform. As further described below, an intermediate electrical waveform generated by the electrical waveform generator 204 and provided to the power-delivery circuitry 205 is used to switch ON and OFF, and otherwise control the coupling of the electrical power provided by the input power processing circuitry 203 to the electrodes of the element 250 through the electrical devices, such as switching devices, included in the power-delivery circuitry.

As shown in FIG. 13, electrical waveform generator 204 includes RF source 204A coupled to modulator 204B. RF source 204A may be configured to generate an electrical waveform having a frequency in a range of 10 kHz to 30 MHz, inclusive. Higher frequencies, for example frequencies up to and including 100 MHz, may be generated by the RF source 204A in various embodiments, and even higher frequencies, up to and including 300 gigahertz, may be generated by the RF source in other embodiments. RF source 204A is not limited to generating a waveform having any particular frequency. In some embodiments, RF source 204A generates an electrical waveform having a frequency of 6.78 Mhz. The frequency generated by RF source 204A may be set based on a determination in some embodiments with respect to the type of fluid, such a saline or water, and/or by the arrangement of the electrodes, such as electrodes 255 and return electrode 256, that the control unit is being configured to heat using non-contact RF heating. Further, the shape and the configuration of the waveform generated by RF source is not limited to any particular shape, and in some embodiments is a sine wave or similar shaped waveform. However, the shape and configuration of the electrical waveform generated by RF source 204A is not limited to a sine wave or similar shaped waveform, and may comprise a square wave, a sawtooth shaped waveform, a triangular shaped waveform, or any other waveform that provides a varying voltage over time.

The type of circuitry utilized by RF source 204A to generate the electrical waveform is not limited to any particular type of circuitry or to any particular technique for generating an electrical waveform. In some embodiments, RF source 204A includes one or more high speed timers configured to generate a varying voltage output signal. In various embodiments, RF source 204A includes a voltage-controlled oscillator, or some other type of oscillator, configured to generate a varying voltage output signal. Other types of circuitry and techniques may be utilized as part of RF source 204A to generate the electrical waveform having a varying voltage output and are contemplated for use as embodiment(s) of the RF source included in control unit 201.

As shown in FIG. 13, an output of RF source 204A is coupled to modulator 204B. Modulator 204B is configured to receive the electrical waveform generated by RF source 204A, and to modulate the electrical waveform to controllably generate an intermediate electrical waveform based on the electrical waveform received from the RF source. In various embodiments, modulator 204B is configured to produce a waveform by switching ON and switching OFF the electrical waveform received from the RF source 204A to produce a pulsed output waveform as the intermediate electrical waveform that is output from the modulator. The pulsed output waveform may comprise cycles having an overall time period including a first time period where the electrical waveform received from the RF source is switched ON, and a second time period following the first time period wherein the RF electrical waveform from the RF source is switched OFF. The overall time period for each cycle of the pulsed output waveform is not limited to a particular time period, and may be 8.3 milliseconds, or a time period less than or greater than 8.3 milliseconds for example in a range of 1 to 100 milliseconds, inclusive. In some embodiments, the duty cycle of the pulsed output waveform may be varied over a range from zero to one hundred percent, and in some embodiments may include a duty cycle of fifty percent. In various embodiments the timing of the switching from an ON state to an OFF state and/or from the OFF state to the ON state corresponds with a zero-crossing voltage level of the electrical power being provided to the power-delivery circuitry by the input power processing circuitry 203. Using switching timing corresponding to the zero-crossing voltage level may reduce stress on the switching devices including in the power-delivery circuitry 205 and may help reduce or eliminate issues related to power factor correction and the incoming electrical power being provided to the control unit 201 by power lines 202. Variations in time period, the duty cycle, or both the time period and the duty cycle of the pulsed output waveform that may be generated as an output from modulator 204B may be controlled and varied in order to control the overall amount of electrical energy that is to be delivered to the electrodes of a non-contact RF heating element, such as element 250, that is being regulated by the intermediate electrical waveform as further described below.

In addition to or instead of controlling the frequency of the electrical waveform provided by RF source 204A, modulator 204B may be configured to variably control a maximum voltage level or a voltage range, such as peak-to-peak voltage, of the electrical waveform received from the RF source. For example, modulator 204B may variably increase or decrease the amount of voltage variation, including varying a maximum voltage level or varying a voltage range (peak-to-peak voltage) of the electrical waveform received by the modulator from RF source 204A. The variations in the voltage level(s) generated by modulator 2049 may then be provided as the intermediate electrical waveform that is output from the modulator. Controlling variations in the voltage levels of the intermediate electrical waveform output by modulator may be used to control the overall amount of electrical energy that is to be delivered to the electrodes of a non-contact RF heating element, such as element 250, that is being regulated by the intermediate electrical waveform as further described below.

In some embodiments, modulator 204B may be configured to modulate the electrical waveform received from the RF source 204A by varying the frequency of the electrical waveform to generate the intermediate electrical waveform that is then provided as an output from the modulator. Controlling variations in the frequency of the intermediate electrical waveform that is being output by the modulator may be used to control the overall amount of electrical energy that is delivered to the electrodes of a non-contact RF heating element, such as element 250, that is being regulated by the intermediate electrical waveform as further described below.

As shown in FIG. 13, an output from modulator 204B is coupled to an input of power-delivery circuitry 205. In addition, electrical power output lines 220 are provided as electrical outputs from input power processing circuitry 203 and are coupled to power-delivery circuitry 205, Electrical power output lines 220 are configured to couple an electrical power source, for example which has been processed and provided by input power processing circuitry 203, to power-delivery circuitry 205. In various embodiments, the electrical power provided by power output line 220 is controllably output by power-delivery circuitry 205 based on and controlled by the intermediate electrical waveform received by the power-delivery circuitry from modulator 2049. In various embodiments, power-delivery circuitry 205 includes one or more electrical switching devices, such as a field-effect transistor (FET), such as but not limited to gallium nitride (GaN) devices, and/or metal-oxide-semiconductor field-effect transistors (MOSFET), such as but not limited to Silicon Carbide (SiC) or silicon MOSFETS. These devices may be configured to act as switching devices to switch ON and thus couple electrical power provided by power lines 220 to the power-delivery circuitry to the outputs of the power-delivery circuitry coupled to electrode output terminal 206 (OUT 1) and the electrode return terminal 207.

The switching devices included in the power-delivery circuitry 205 are also configured to be controllably switched OFF, and thus to disconnect the electrical power being provided by power lines 220 to the power-delivery circuitry from the outputs of the power-delivery circuitry coupled to electrode output terminal 206 (OUT 1) and the electrode return terminal 207. In various embodiments, during the periods of time when the switching devices are switched ON, the switching devices included in the power-delivery circuitry 205 may be further controlled by the intermediate electrical waveform received from the electrical waveform generator 204 to vary for example the voltage level being provided at the electrode output terminal coupled to the switching device(s) in order to provide a varying voltage output waveform having variations corresponding to the variations of the intermediate electrical waveform to the electrodes of element 250. As further described below, the various parameters of the intermediate electrical waveform generated by the electrical waveform generator 204 may be controlled by input signals provided to the electrical waveform generator by control circuitry 210. In various embodiments, electrical waveform outputs provided to the electrodes of element 250 as an output from the power-delivery circuitry 205 and as controlled by the intermediate electrical waveform generated by electrical waveform generator 204 may be configured to produce non-contact radio-frequency heating of a fluid flowing through passageway 252 of the element.

As shown in FIG. 13, control circuitry 210 may dude a computer system, such as a microprocessor and associated computer circuitry, that may include computer memory coupled to one or more computer processors, illustratively represented in FIG. 13 as memory 212 and processor 211, respectively. Memory 212 may store instructions and one or more parameter values that processor 211 may operate on to control the operation of control unit 201. For example, memory 212 may store one or more values corresponding to desired temperature outputs or to an acceptable range of temperature outputs for the heated fluid flow exiting the element 250. Processor 211 may use this desired temperate value, or the acceptable temperature range of values, to determine how to control the output of electrical energy provided at electrode output terminal 206 in order to control the heating of the fluid flow through element 250. Processor 211 may use inputs provided to control unit 201, such as temperature sensor signals provided by one or more temperature sensors 257, flow sensor inputs provided by flow sensor 259, ambient temperature inputs provided by ambient temperature sensor 264, and/or other inputs or parameters values for use in various algorithms used to regulate the generation of the intermediate electrical waveform, which in turn is used to control the power-delivery circuitry to provide electrical output waveforms to be provided to electrode output terminal 206, and thus used to regulate the heating of the fluid flow through passageway 252 and element 250 in a desired manner.

Control circuitry 210 may utilize one or more techniques to control the overall level of electrical energy provided to the electrodes of a non-contact radio-frequency heating element, such as element 250, and thus control the heating of a fluid flowing through the heating element. In various embodiments, control circuitry 210 may provide one or more control signals to input power processing circuitry 203. These control signals may allow the control circuitry to modify one or more parameters of the power that is to be or is being provided by the input power processing circuitry to the power-delivery circuitry 205. In various embodiments, control circuitry 210 may provide one or more control signals to electrical waveform generator 204 configured to control and/or vary the frequency of the intermediate electrical waveform being provided as an output from the electrical waveform generator. Varying the frequency of the electrical waveform generator's intermediate electrical waveform may change the overall impedance of the circuit that includes a fluid flowing past and/or positioned between electrodes of a non-contact radio-frequency heating element, and thus control the overall heating of the fluid. In various embodiments, control circuitry 210 may provide one or more control signals to electrical waveform generator 204 that are configured to control and/or vary one or more of voltage levels, such as peak voltage and/or peak-to-peak voltage, of the electrical output waveform provided as an output from the power-delivery circuitry 205. Varying one or more voltage levels of the intermediate electrical waveform being provided as an output from the electrical waveform generator 204 may change the overall level of electrical power being delivered by the power-delivery circuitry 205 to the electrodes of a non-contact radio-frequency heating element, such as element 250, and thus control the overall heating of the fluid passing through the non-contact radio-frequency heating element.

In various embodiments, control circuitry 210 may provide one or more control signals to electrical waveform generator 204, for example to modulator 204B, that are configured to control and/or generate a pulsed output of the intermediate electrical waveform provided as an output from electrical waveform generator 204 to the power-delivery circuitry 205, and thus control a duty cycle for the application of electrical power to the electrodes of a non-contact radio-frequency heating element, such as element 250. Controlling a duty cycle of the electrical power being provided as an output from the power-delivery circuitry 205 may change the overall level of electrical power being delivered to the electrodes of a non-contact radio-frequency heating element, and thus control the overall heating of the fluid passing through the non-contact radio-frequency heating element.

Various embodiments of control unit 201 include a user interface 214 communicatively coupled to control circuitry 210. User interface 214 may be configured to allow electrical communications, for example but not limited to communication utilizing a RS-232 format, between control circuitry 210 and one or more other computer systems, such as computer system 265 as illustrated in FIG. 13, which are external to control unit 201. In various embodiments, computer system 265 may be used to download programming and/or parameter values to control circuitry 210, which may then be stored in memory 212 and operated on by processor 211. Programming parameters may include information related to the type of non-contact radio-frequency heating element and/or the arrangement of electrodes that the control unit is being configured to be coupled to as part of a non-contact radio-frequency heating system, such as system 200. In various embodiments, parameters, such as a desired temperature or an acceptable temperature range of the output of heated fluid passing through a non-contact radio-frequency heating element that is electrically coupled to control unit 201 may be provided through user interface 214 to control circuitry 210. Other information, such as but not limited to the distance along a conduit extending from the output of the non-contact radio-frequency heating element to the point where the fluid is introduced into a patient may be provided to control circuitry 210 through user interface 214. Such information may be utilized by control circuitry 210 to determine the overall heating regiment that may be applied to heating a fluid flow that is passing through the element coupled to the control unit 201 by factoring in the amount of cooling that is likely to occur after the fluid exits the element and before introduction into the patient. Additional information that may be provided to control circuitry 210 through user interface 214 may include information related to the types and numbers of sensors included as part of a non-contact radio-frequency heating unit that the control unit 201 is to be coupled to, and the type of fluid that is being passed through the element for heating purposes. In various embodiments, user interface 214 may also be configured to output information from control circuitry 210 to the external computer systems that may be coupled to the user interface, such as temperature readings, temperate profiles related to a heating process performed by the control unit 201, and/or output of data related to the control parameters that were utilized by the control unit to produce these temperate reading and temperature profiles.

In various embodiments, control unit 201 may include a temperature output 216 that is electrically coupled to control circuitry 210. Temperature output 216 may provide an output signal, such as a voltage output, that is indicative of a current temperature value for a fluid that is being heated by or at least flowing through the non-contact radio-frequency heating element coupled to control unit 201. The temperature output signal may in some embodiments be provided to a display device configured to visually display a value corresponding to the temperature indicated by the signal provided at the temperature output 216.

Control unit 201 may provide various features and perform various functions related to safety and regulation of a non-contact radio-frequency heating system such as system 200. For example, various types of shielding may be provided to limit or eliminate electromagnetic radiation associated with the higher frequencies that may be generated by and transmitted through the system. In various embodiments, certain fault conditions may be monitored for, and when detected may result in a shutdown and/or a power down of one or more portions of the control unit. For example, an overvoltage and/or an over current condition occurring in the power input power processing circuitry 203, electrical waveform generator 204, and/or power-delivery circuitry 205 may be monitored for, and if any voltage or current levels exceed acceptable levels, one or all of these portions of the control unit 201 may be powered down. In various embodiments, the temperature of one or more switching devices, such as MOSFETs, that may be included in power-delivery circuitry 205 may be monitored, and if these temperature(s) exceed acceptable limits, the power-delivery circuitry 205 may be powered down. In various embodiments, a parameter related to a maximum fluid temperature sensed by one or more temperature sensors sensing temperatures of the fluid at or passing through the non-contact radio-frequency heating element coupled to the control unit may be monitored, and if the fluid temperature(s) exceeds any threshold level(s) set for fluid temperature, the control unit may shut down the electrical waveform generator and/or power-delivery circuitry of the control unit so that the electrical output waveform is disconnected from the electrode output terminal(s) of the control unit and is no longer being applied to the electrodes of the non-contact radio-frequency heating element. In various embodiments, a flow level or volume of fluid flow passing through the non-contact radio-frequency heating element is monitored, and if no flow is detected, or for example a minimum level of fluid flow is not detected, the control unit may be configured to stop providing electrical energy to the electrodes of the non-contact radio-frequency heating element, and thus cease any further heating of the fluid until and/or unless a fluid flow is detected, or the minimum level of fluid flow is re-established through the non-contact radio-frequency heating element.

In various embodiments the control circuitry 210 performs the monitoring and alarm function, and controls output signals to the electrical waveform generator 204 and/or the power-delivery circuitry 205 to power down or shut down portions of the control unit when an unacceptable, fault, or alarm condition is detected. In various embodiments, other devices, such as fuses and/or circuit breaker, which may or may not be controlled by the control circuitry 210, may provide protection, such as protection against electrical overloads within the control unit 201 and/or associated with the electrical power being provided to the non-contact radio-frequency heating element by the control unit and/or to the control unit from any electrical power input sources coupled to lines 202.

The overall wattage level of electrical energy provided by control unit 201 to a RF heating element, such as element 250, is not limited to any particular wattage, and in various embodiments is configured and controlled based on the particular application, such as the type of fluid being processed, the amount of heating of the fluid that is required, and/or the configuration of the RF heating element itself. In various embodiments, a control unit, such as control unit 250, is configured to provide an overall wattage level in a range of 0 to 500 watts of electrical power in a controlled manner to a RF heating element. Embodiments may include higher wattage levels for example up to and including 2000 watts or more, again depending on the application. In various arrangements, the application of the electrical energy to the fluid as part of the RF heating process may generate bubbles, such as gas bubbles, in the fluid. In various embodiments, operations utilizing the RF heating element may include positioning the exit end of the element in a vertical or upward orientation to: 1) allow for all bubbles to exit the tubing, 2) for preventing any new bubbles from getting trapped, 3) and/or allow any generated gas to escape. In various embodiments, one or more bubble sensors may be incorporated into a RF heating system, such as system 200, to detect the presence of gas bubbles in the fluid being heated, and to provide an output signal to the control unit 201 indicative of the presence or absence of bubbles that may be detected in the fluid. An embodiment of a bubble sensor may comprise a light source, such as but not limited to a laser light source, and a photo detector, such as but not limited to a photodiode, configured to detect the light provided by the light source. The bubble detector may be configured to provide an output signal that is indicative of the presence or absence of bubbles in the fluid. In various embodiments, the bubble sensor may be built into the RF heating element, and/or may be incorporated into the fluid output conduit, such as fluid output conduit 254 as shown in FIG. 13, for example as sensor 259 as shown in FIG. 13. In various embodiments, the output signal from the bubble sensor may be received by control circuitry included in the control unit, such as control circuitry 210, and used to regulate the level of electrical energy being applied to the fluid that is flowing through or is contained within the RF heating elements. In various embodiments, an output signal from the bubble sensor may be processed by the control circuitry, causing the control circuitry to reduce the level of electrical energy being provided to the RF heating element, and thus reduce or eliminate the formation of bubbles in the fluid. In various embodiments, the detection of bubbles in the fluid may be considered an alarm condition, and when bubbles are detected, for example based on the output signal generated by a bubble sensor, the control circuitry of the control unit may be configured to shut down or otherwise stop providing electrical energy to the RF heating element, and/or may output an alarm signal, for example to an external computer system such as computer system 265, intended to alert a system user, such as a medical technician or operator, of the detection of the bubbles in the fluid being processed by the RF heating element.

Figure 14A:
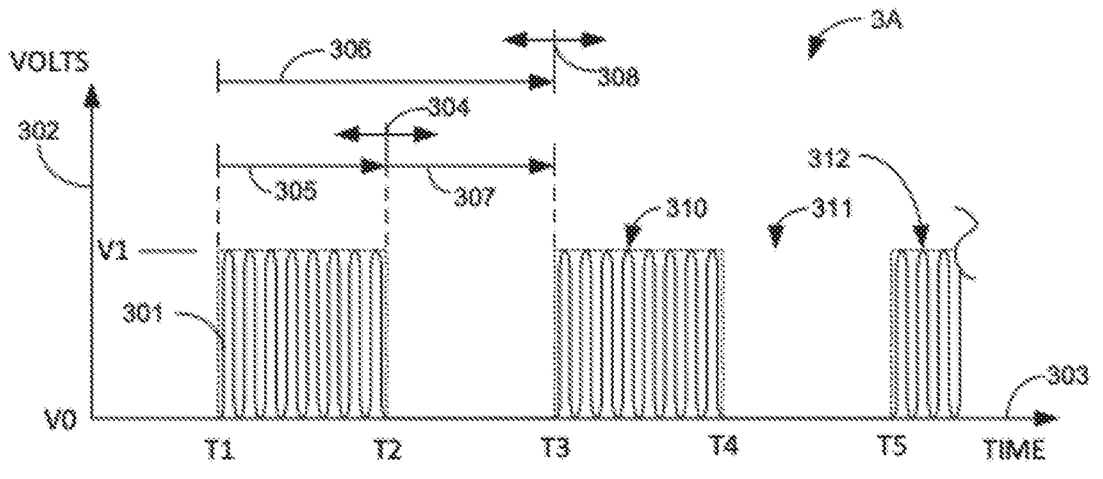
FIGS. 14A-14C illustrate graphical depictions of various electrical output waveforms that may be generated and applied to one or more electrodes of a non-contact radio-frequency heating element according to at least one embodiment.
Figure 14B:
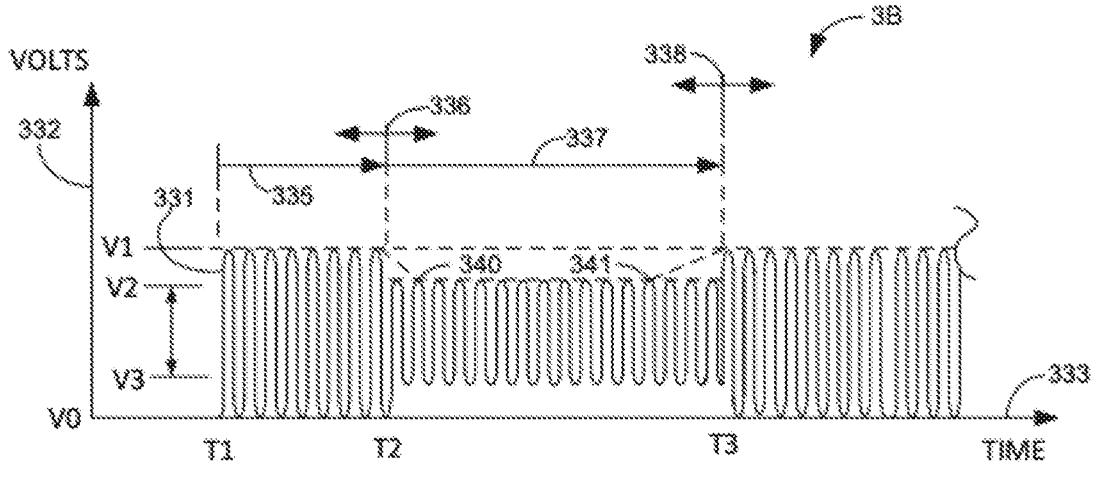
Figure 14C:
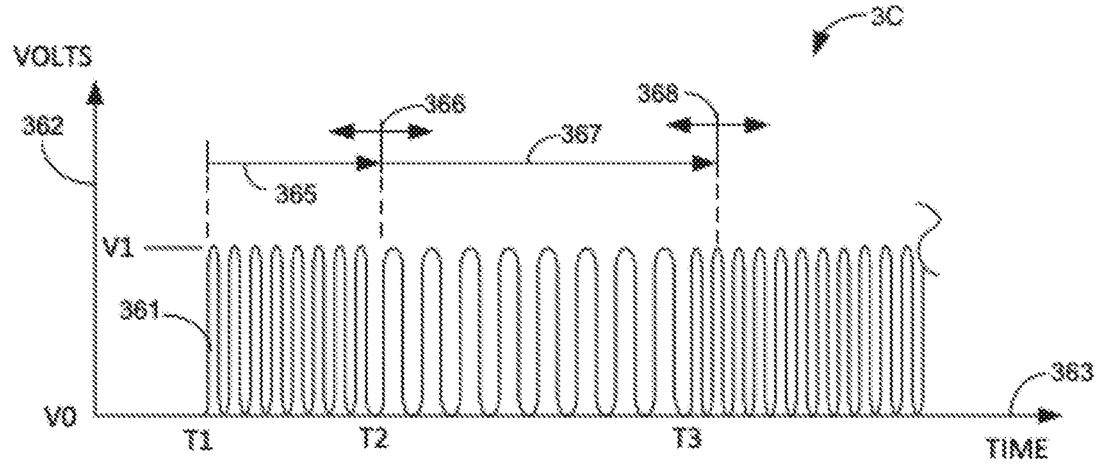

FIGS. 14A-14C illustrate graphs 3A, 3B, and 3C, respectively, of various electrical output waveforms that may be generated and applied to one or more electrodes of a non-contact radio-frequency heating element according to at least one embodiment. The variations in the waveforms illustrated by each of graphs 3A, 3B, and 3C, alone or in some combination, may be used to control the electrical power delivered by a control unit, such as control unit 201 (FIG. 13), and thus provide control over the heating of a fluid that is flowing through or that is contained within a non-contact radio-frequency heating element, such as element 250 (FIG. 13) that is coupled to receive the electrical power provided by the control unit.

FIG. 14A illustrates a graph 3A of an electrical output waveform 301 that may be generated and applied to one or more electrodes of a non-contact radio-frequency heating element according to at least one embodiment. Graph 3A includes a vertical axis 302 representing voltage levels, and a horizontal axis 303 representing time. Waveform 301 as illustrated in FIG. 14A is a sine wave having a varying voltage level extending between voltage level V0 and voltage level V1 at some predetermined frequency. In some embodiments, the frequency of waveform 301 is 6.78 MHz. However, the frequency of waveform 301 is not limited to 6.78 MHz, or to a particular frequency, and in various embodiments may be any frequency in a range of 10 kHz to 30 MHz, inclusive. Other embodiments of waveform 301 may be as high as 100 MHz, or up to and including 300 GHz. Further, waveform 301 is not limited to a waveform comprising a sine wave, and in various embodiments may be a waveform that is not a sine wave, for example a square wave, a sawtooth shaped waveform, or a triangular shaped waveform.

As shown in FIG. 14A, prior to time T1, waveform 301 is maintained at voltage level V0, but is turned ON at time T1, and remains in an ON state over the time period represented by arrow 305 until time T2. At time T2, waveform 301 is switched to an OFF state, and remains at the V0 voltage level over a second time period represented by arrow 307 that begins at time T2 and ends at time T3. The combination of the first time period 305 and the second time period 307 extends from time T1 to time T3 and is represented by time period illustrated by arrow 306. The time period represented by arrow 306 represents the time period for one ON/OFF cycle of waveform 301, wherein during the first time period 305 waveform 301 oscillates at a predefined frequency, and during the second time period 307 waveform 301 is held at a constant voltage level represented by voltage V0. As such, the relative length of the first time period compared to the relative time period represented by the second time period (arrow 307) represents a duty cycle for the ON/OFF switching of waveform 301 over period 306. In various embodiments, the peak-to-peak voltage value for waveform 301 may include a range of 5 to 20,000 volts, inclusive.

Following time T3, a subsequent time period 310 may include waveform 301 switched to an ON state, extending to time T4 as represented by arrow 310, wherein at time T4 waveform 301 is switched back to the OFF state for a time period represented by arrow 311 extending from time T4 to time T5. The time periods 310 and 311 represent another and subsequent ON/OFF switching cycle of waveform 301 having a duty cycle and an overall period that may be adjusted to control the overall amount of electrical power provided during this subsequent cycling of waveform 301. Additional switching cycles, as represented by the partially illustrated time period of at arrow 312, may follow after time T5 and may include variable time periods and/or variable duty cycles as described above for the previous ON/OFF switching cycles of waveform 301.

The ON/OFF switching of waveform 301 may represent a switching of an electrical power output from an electrical waveform generator (e.g., electrical waveform generator 204, FIG. 13), that is then applied to a power-delivery circuitry, such as power-delivery circuitry 205 (FIG. 13). Controlling the switching on and off of the power-delivery circuitry (e.g., power-delivery circuitry 205, FIG. 13) may result in delivery of a set of ON/OFF pulses of electrical power provided for example by input power processing circuitry (203—FIG. 13) in the form of electrical waveform corresponding to waveform 301 to one or more electrodes of a non-contact radio-frequency heating element to control heating of a fluid flowing through or contained within the non-contact radio-frequency heating element. As shown in FIG. 14A, the overall time included in time period 306 may be varied, and represented by the double arrows 308 coupled to line at time T3, to increase or decrease the rate at which the ON/OFF cycles are provided to the electrodes. In addition, the duty cycle as shown in FIG. 14A is represented a being a fifty-percent duty cycle, with the first time period (arrow 305) having an equal time span as the second time period (arrow 307), so that the waveform is providing a varying voltage for half the time period 306, and is providing no voltage level during the second half of time period 306. However, as represented by the double arrows 304 coupled to the line at time 12, the relative time spans of the first time period and the second time period may be varied in order to change the duty cycle of the waveform 301. Increasing the duty cycle, that is, extending the first time period relative to the second time period, would increase the relative time during time period 306 when waveform 301 is providing electrical power, and decreasing the duty cycle would decrease the relative time period 306 during which waveform 301 is providing electrical power. By adjusting either the period 306, the duty cycle of period 306, or both the period of 306 and the duty cycle of waveform 301, control over the amount of electrical power, and thus over the amount of heating of a fluid flowing through or contained within a non-contact radio-frequency heating element receiving the electrical power provided by waveform 301 may be controlled, FIG. 14B illustrates a graph 3B of an electrical output waveform 331 that may be generated and applied to one or more electrodes of a non-contact radio-frequency heating element according to at least one embodiment. Graph 3B includes a vertical axis 332 representing voltage levels, and a horizontal axis 333 representing time. Waveform 331 as illustrated in FIG. 14B is a sine wave having a varying voltage level extending between voltage level V0 and voltage level V1 at some predetermined frequency over a first time period 335 extending from time T1 to time T2, and a varying voltage level extending between voltage level V2 and voltage level V3 over a second time period 337 extending from time T2 to time T3. In some embodiments, the frequency of waveform 331 is 6.78 MHz. However, the frequency of waveform 331 is not limited to 6.78 MHz, or to a particular frequency, and in various embodiments may be any frequency in a range of 10 kHz to 30 MHz, inclusive, or in some embodiments up to 100 MHz and in still other embodiments up to 300 GHz. Further, waveform 331 is not limited to a waveform comprising a sine wave, and in various embodiments may be a waveform that is not a sine wave, for example a square wave, a sawtooth shaped waveform, or a triangular shaped waveform.

As shown in FIG. 14B, the variations in the peak-to-peak voltage levels of waveform 331 during time period 335 are larger than the variations in the peak-to-peak voltage levels for waveform 331 during time period 337. In various embodiments, waveform 331 is an intermediate electrical waveform generated by an electrical waveform generator, such as electrical waveform generator 204 (FIG. 13) and is used to control the power-delivery circuitry that is electrically coupled to the electrodes of a heating element, such as element 250 (FIG. 13), by controlling the power-delivery circuitry to provide an electrical power to the electrodes having a waveform that corresponds to waveform 331. As such, during time period 335 waveform 331 will deliver more electrical power on average for a given period of time compared to amount of electrical power delivered on average for a same given period of time while providing the variation in waveform 331 as illustrated for time period 337. By controlling the overall peak-to-peak voltage level of waveform 331, control over the amount of electrical power, and thus over the amount of heating of a fluid flowing through or contained within a non-contact radio-frequency heating element receiving the electrical power provided by waveform 331 may be controlled. As shown in graph 3B, the point in time where the voltage variation is changed at time T2 can be varied back or forward relative to time axis 333, thus switching the voltage variation represented by time period 337 to an earlier or a later time. Similarly, the time T3 where the voltage variation of waveform 331 is again switched to a different level for the peak-to-peak voltage may be varied, as illustrated by arrows 338, relative to time axis 333.

As further illustrated in FIG. 14B, at time T3 the peak-to-peak voltage variation of waveform 331 returns to a level extending between V0 and V1, which comprises a higher peak-to-peak voltage value for waveform 331 compared to the peak-to-peak voltage variations of waveform 331 during time period 337. Thus, waveform 331 provides more electrical power, and thus generates a greater amount of heating of a fluid flowing through or contained within a non-contact radio-frequency heating element compared to the electrical power and heating generated by waveform 331 for a same period of time during time period 337. The time for the change in the variation of the voltage levels between time period 335 and 337 may be configured as a ramp up or a ramp down relative to peak-to-peak voltage levels, as represented by dashed ramp lines 340 and 341. Further, the variation in peak-to-peak voltage levels is not limited to the use of two different voltage levels and may include use of any number of discrete voltage levels, or variation of the peak-to-peak voltage level over a continuous range of values for varying the voltage levels. In various embodiments, the peak-to-peak voltage values for waveform 331 may vary from over a range of 5 to 20,000 volts, inclusive. In addition to varying peak-to-peak voltage, output waveform 331 may be switched ON and OFF in a manner similar to that described above for waveform 301 and graph 3A.

FIG. 14C illustrates a graph 3C of an electrical output waveform 361 that may be generated and applied to one or more electrodes of a non-contact radio-frequency heating element according to at least one embodiment. Graph 3C includes a vertical axis 362 representing voltage levels, and a horizontal axis 363 representing time. Waveform 361 as illustrated in FIG. 14C is a sine wave having a varying voltage level extending between voltage level V0 and voltage level V1 at some predetermined frequency over a first time period 365 extending from time T1 to time T2, and a varying voltage level having a different frequency and extending between voltage level V0 and voltage level V1 over a second time period 367 extending from time T2 to time T3. In various embodiments, the peak-to-peak voltage values for waveform 361 may vary from over a range of 5 to 20,000 volts, inclusive. In some embodiments, at least one of the frequencies represented by waveform 361 over one of time period 365 or 367 is a frequency of 6.78 MHz. However, the frequency of waveform 361 is not limited to 6.78 MHz, or to a particular frequency, and in various embodiments may be any frequency in a range of 10 kHz to 30 MHz, inclusive. Further, waveform 361 is not limited to a waveform comprising a sine wave, and in various embodiments may be a waveform that is not a sine wave, for example a square wave, a sawtooth shaped waveform, or a triangular shaped waveform.

As shown in FIG. 14C, waveform 361 oscillates at a first frequency over time period 365, and then oscillates at a different, lower frequency over time period 367. After time T3, waveform 361 returns to having a frequency the same as the frequency of waveform 361 over time period 365. By varying the frequency of waveform 361, the impedance of the circuit including electrodes and the fluid passing through or contained within a non-contact radio-frequency heating element receiving the electrical power in the form of waveform 361 varies, and thus the total amount of electrical power, and therefore the heating of the fluid may be varied and controlled by the variation of the frequency of waveform 361. For example, in various embodiments waveform 361 is an intermediate electrical waveform generated by an electrical waveform generator, such as electrical waveform generator 204 (FIG. 13), and is used to control the power-delivery circuitry, such as power-delivery circuitry 205 (FIG. 13) that is electrically coupled to the electrodes of a heating element, such as element 250 (FIG. 13) by controlling the power-delivery circuitry to provide an electrical power to the electrodes having a waveform that corresponds to waveform 361. The range of frequency over with the frequency of waveform 361 may be varied is not limited to any particular frequency or range of frequencies and various embodiments includes varying the frequency over a range of frequencies extending from 10 kHz to 30 MHz, inclusive, or in some embodiments up to 100 MHz and in still other embodiments up to 300 GHz.

In various embodiments, the time period during which waveform 361 is provided as having a first frequency illustrated by arrow 365 may be varied, as illustratively indicated by double arrows 366, and/or the time period during which waveform 361 is provided as having a second frequency different from the first frequency, as illustrated by arrow 367 may be varied, as illustratively indicated by double arrows 368. In addition to varying frequency of waveform 361 over different and subsequent time periods, waveform 361 may be switched ON and OFF in a manner similar to that described above for waveform 301 and graph 3A. In the alternative or in addition to switching the waveform 361 ON and OFF, the overall peak-to-peak voltage of waveform 361 may be varied in a same or similar manner as described above with respect to graph 3B and waveform 331.

Figure 15A:
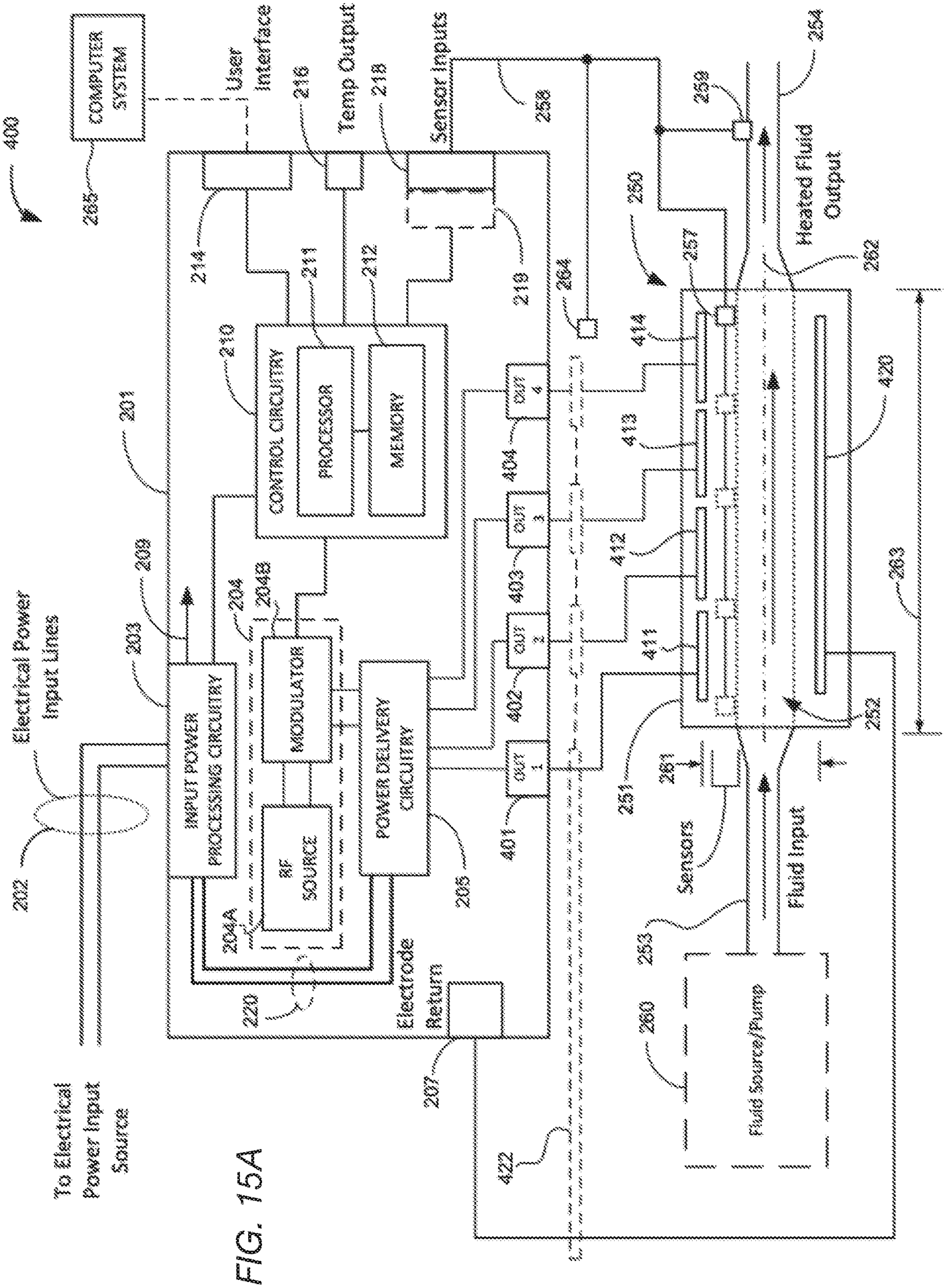
FIG. 15A illustrates a schematic block diagram of a non-contact radio-frequency heating system according to at least one embodiment.

FIG. 15A illustrates a schematic block diagram of a fluid non-contact radio-frequency heating system 400 (hereinafter "system 400") according to at least one embodiment. As shown in FIG. 15A, system 400 includes many of the same devices and electrical circuitry, including a non-contact radio-frequency heating element 250 that is electrically coupled to a non-contact radio-frequency heating control unit 201 (hereinafter "control unit 201"). System 400 may be configured to provide a controlled level of non-contact radio-frequency heating to a flow of fluid passing through element 250 by non-contact radio-frequency heating of the fluid flow using electrical energy provided and controlled by control unit 201 to one or more electrodes included in element 250, as described above with respect to FIG. 13 and system 200. Therefore, the same references numbers are used in FIG. 15A to refer to the same or similar devices as illustrated in FIG. 13 with reference to system 200, with variations and differences between the two systems further described below.

As shown in FIG. 15A and for system 400, control unit 201 includes four separate electrode output terminals, including output 1 (401), output 2 (402), output 3 (403), and output 4 (404). Each of the electrode output terminals is coupled to power-delivery circuitry 205 and is configured to receive an electrical output waveform provided to the electrode output terminal from the power-delivery circuitry. In addition, each of the electrode output terminals 401, 402, 403, and 404 is coupled to a respective one of the separate electrodes 411, 412, 413, and 414 included in body 251 of non-contact radio-frequency heating element 250. As shown in FIG. 15A, electrode output terminal 401 is coupled to electrode 411, electrode output terminal 402 is coupled to electrode 412, electrode output terminal 403 is coupled to electrode 413, and electrode output terminal 404 is coupled to electrode 414. Each of these electrodes individually or together, in combination with return electrode 420, may be referred to as a set of electrodes.

In various embodiments, each of electrodes 411, 412, 413, and 414 is electrically isolated from one another, and positioned above and proximate to passageway 252 of non-contact radio-frequency heating element 250. A return electrode 420 is electrically isolated from each of the electrodes 411, 412, 413, and 414, and is positioned below passageway 252 on an opposite side of the passageway relative to electrodes 411, 412, 413, and 414. As shown in FIG. 15A, each electrode 411, 412, 413, and 414 extends parallel to longitudinal axis 262, and along a portion of the length dimension 263 of the element 250 that is different from the portion of the length dimension 263 over which any of the other electrodes extend. Return electrode 420 may extend parallel to electrodes 411, 412, 413, and 414, and extend over a length dimension along the longitudinal axis 262 that includes all of the length dimension extended over by each of the electrodes 411, 412, 413, and 414.

In various embodiments, electrode conductor wiring 422 may include shielding coupled to return electrode 420, and to electrode return terminal 207 of control unit 201, wherein separate sets of wiring may be utilized to couple and/or shield each individual electrode 411, 412, 413, and 414 along with a respective return conductors for coupling the respective electrode and return electrode 420 to control unit 201. In various embodiments, instead of being formed as a single electrode, return electrode 420 may comprise individual electrodes (not specifically shown in FIG. 15A), each of the individual return electrodes positioned opposite a respective one of electrodes 411, 412, 413, and 414, thus forming four sets of individual electrode/return electrode pairs. Each of electrodes 411, 412, 413, and 414, along with an individual return electrode, may be referred to as a set of electrodes.

In various embodiments, electrodes 411, 412, 413, and 414, along with return electrode 420, are generally formed having a planar flat shape. However, embodiments of the electrodes and the return electrode or return electrodes are not limited to having a planar flat shape, and may for example have a curved arch-shape the extends at least partially around the longitudinal axis 262 at some radial distance from the longitudinal axis while remaining electrically isolated from direct contact with all other electrodes included in the element 250.

In various embodiments, control unit 201 may be configured to individually control an electrical output waveform provided to each of the electrode output terminals, 401, 402, 403, and 404, thus providing individually controlled outputs to each of the electrodes 411, 412, 413, and 414, respectively. In various embodiments, control unit 201 may operate all of the electrode output terminals 401 at the same time with respect to a switched ON and OFF state for application of an electrical output waveform to the electrodes. In various embodiments, control unit 201 may operate these ON and OFF states to individually control the output of an electrical output waveform to the respective electrode output terminals, and thus to the electrodes of the element 250 on an individual basis, wherein one or more of the electrode output terminals may be switched to an OFF state while other ones of the electrode output terminals are switched to an ON state. In various embodiments, an added number of temperature sensors, for example five temperature sensors as illustrated in FIG. 15A, may be included in the non-contact radio-frequency heating element 250 and configured to generate sensor output signals related to sensed temperatures at or proximate to each of the electrodes. The sensor output signals from the temperature sensors are coupled to the control unit 201 through sensor input 218 to allow the control unit 201 to determine temperature gradients that may exist over the length of the element 250, and thereby provide more resolution with respect to heating control applied through the electrical output waveforms being applied to the individual electrodes 411, 412, 413, and 414.

In various embodiments, different electrical output waveforms, such as but not limited to the electrical output waveforms described above with respect to FIGS. 14A-14C, may be applied to one or more of the electrode output terminals 401, 402, 403, and 404 at any given time to control the heating of a fluid passing through or contained within passageway 252. For example, electrode output terminal 401 may receive an electrical output waveform continuously, wherein one or more of electrode output terminals 402, 403, and/or 404 may receive a pulse electrical output waveform such as waveform 301 as illustrated and described with respect to FIG. 14A. Varying the waveforms, and thus the amount of heating provided by the electrodes at different positions relative to the length dimension 263 of the element 250 may provide a more uniform heating in a smaller overall length dimension for element 250 compared to a single electrode embodiment of the element. Other variations of the control scheme for multiple electrodes provided in a non-contact radio-frequency heating element are possible and are contemplated for use by system 400 as illustrated and described with respect to FIG. 15A. Further, embodiments of system 400 are not limited to having a particular number of electrode output terminals for controlling electrodes, such as the four electrode output terminals as illustrated in FIG. 15A, and may include embodiments that comprise less electrodes, such as two or three electrode terminal outputs, or more electrode terminal outputs, such as five or more electrode terminal outputs, that may be configured to control multiple electrode or multiple electrode sets provided within or as part of an electric heating element configured to be electrically coupled to the control unit.

Figure 15B:
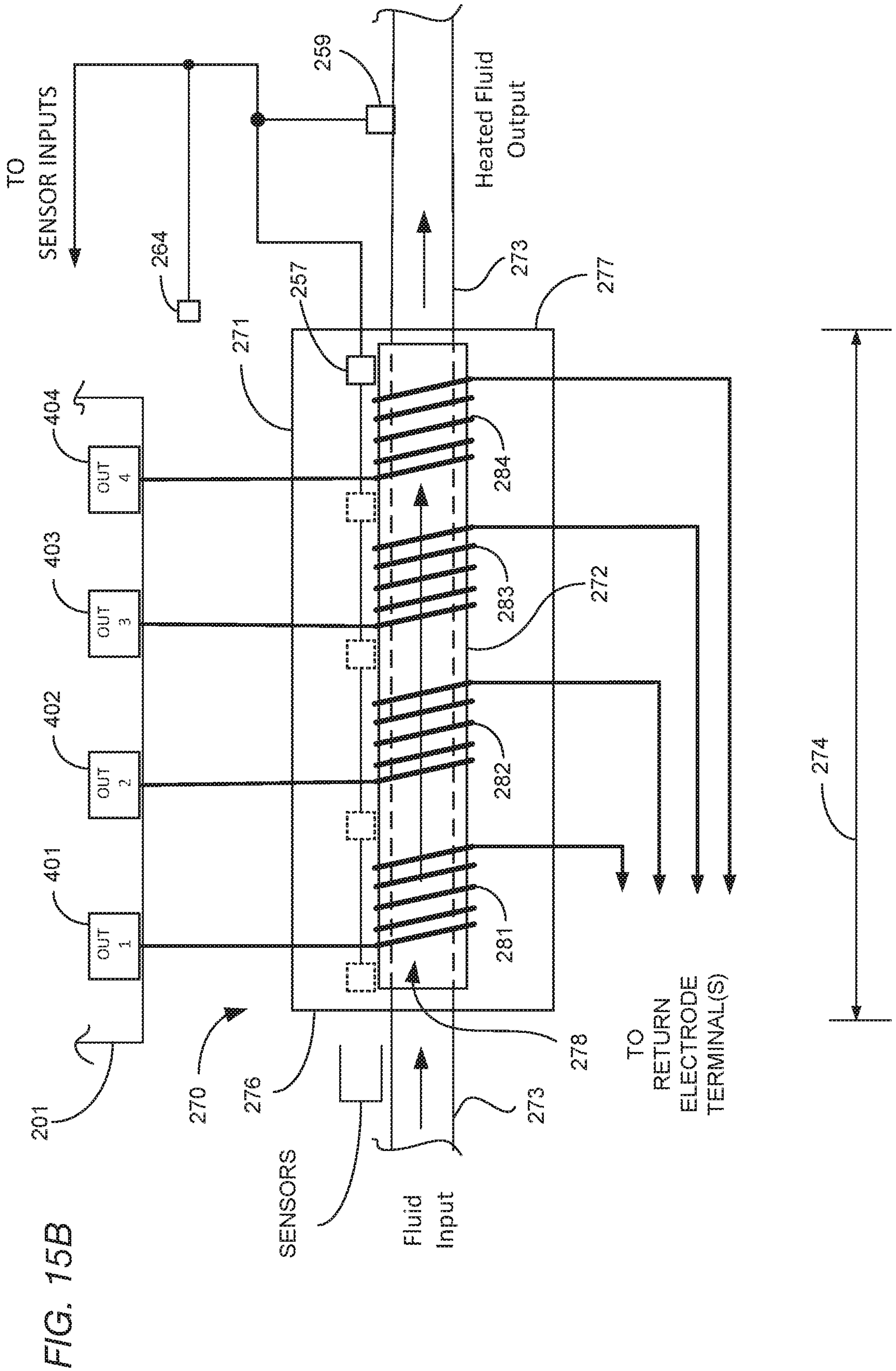
FIG. 15B illustrates a schematic block diagram including a non-contact radio-frequency heating element according to at least one embodiment.

FIG. 15B illustrates a schematic block diagram including a non-contact radio-frequency heating element 270 according to at least one embodiment. As shown in FIG. 15B, non-contact radio-frequency heating element 270, (hereinafter "element 270"), includes a heating element body 271 (hereinafter "body 271"), having an outer tube 272 extending through at least a portion of body 271, and an inner tube 273 that is at least partially encircled by outer tube 272. Inner tube 273 extends through both the outer tube 272 and body 271. Inner tube 273 extends through a first end 276 of body 271, through the body along a length dimension 274 of the body, and out of a second end 277 of the body that is opposite first end 276. Inner tube 273 is configured to provide a passageway 278 for a flow of fluid through body 271. In various embodiments, inner tube 273 is formed from an electrically insulative material, such as a plastic material, although embodiments of the inner tube are not limited to any particular type of electrically insulative material. In various embodiments, outer tube 272 is formed from a material such as metal, stainless steel, or other metallic material that allows the inductive fields generated by the inductive coils 281, 282, 283, and 284 to be imposed on the area within inner tube 273, including passageway 278. However, embodiments of the material or type of materials that may be used to form outer tube 272 are not limited to a particular type of material, and any material or type of materials compatible with the operation of the inductive coils in heating a fluid that is flowing through or contained within passageway 278 may be used to form the outer tube. As further shown in FIG. 15B, a set of inductive coils 281, 282, 283, and 284 are wound around outer tube 272 and spaced, respectively, along the longitudinal dimension of the outer tube. Each of the inductive coils 281, 282, 283, and 284 is electrically coupled to a respective one of the electrode output terminals of control unit 201, and to the return electrode terminal(s) of control unit 201. As shown in FIG. 15B, inductive coil 281 is coupled to electrode output terminal 401 (OUT 1), inductive coil 282 is coupled to electrode output terminal 402 (OUT 2), inductive coil 283 is coupled to electrode output terminal 403 (OUT 3), and inductive coil 284 is coupled to electrode output terminal 404 (OUT 4) of control unit 201. Each of the inductive coils is also electrically coupled to one or separate ones of the return electrode terminals included as part of control unit 201.

The windings forming inductive coils 281, 282, 283, and 284 are not limited to any particular type of winding, or to any particular number of turns per used to form each coil, or to any particular type of material used to form the inductive coils. In some embodiments, each of inductive coils 281, 282, 283, and 284 comprises a same type of electrical conductor, such as a conductive metal such as copper, aluminum, silver, or gold, which may be used to form each winding, and a same number of turns of the electrical conductor. However, embodiments of the element 270 are not limited to having four coils in number, and may have more or less than four coils, including having just a single (one) coil. Further, embodiments of element 270 are not limited to having each of a plurality of coils included in the element comprising a same type of coil winding. For example, one or more of a plurality of coils included in element 270 may include more or less turns of winding of the electrical conductor used to form the inductive coil, and/or may be formed from a different electrical conductor, for example a different gauge of wire or other conductive element used to form the inductive coil(s).

In operation, control unit 201 may be configured to provide one or more electrical output waveform(s) to inductive coils 281, 282, 283, and 284 in order to generate an electromagnetic field in the area surrounding each inductive coil, including within the area surrounding each inductive coil included within passageway 278 of inner tube 273. The electromagnetic field(s) generated by inductive coils 281, 282, 283, and 284 may be configured to produce heating for fluid that is flowing through or contained within the passageway 278. In various embodiments, control unit 201 applied a same electrical output waveform to each of inductive coils 281, 282, 283, and 284 at or over a same time period, including applying a pulsed electrical output waveform to each of the inductive coils 281, 282, 283, and 284 at a same period and same phase relative to the pulses of the electrical output waveform. However, embodiments may include control unit 201 providing different electrical waveform(s) to one or more of the inductive coils 281, 282, 283, and 284 at a same or at different times, wherein various combinations of the inductive coils 281, 282, 283, and 284 may be energized and de-energized at different time relative to one another and energized using different electrical output waveforms at a same or different time relative to the electrical waveform(s) being applied to energize other ones of the inductive coil. By varying and controlling the electrical waveform(s) used to energize the inductive coils 281, 282, 283, and 284, and/or the timing of the energization of each of the inductive coils 281, 282, 283, and 284, either individually or together in some combination, the heating of the fluid that is flowing through or contained within passageway 278 may be controlled.

Embodiments utilizing element 270 may be configured and operated to provide any of the features and to perform any of the functions related to heating, sterilization, or other processing of fluid as described throughout this disclosure, and any equivalents thereof. For example, as shown in FIG. 15B element 270 includes any combination of one or more temperatures sensors 257, one or more flow sensors 259, and/or one or more ambient temperature sensors 264. Output signals provided by these sensors, when present, may be coupled to control unit 201 and the corresponding information provided by the output signals incorporated into the temperature regulation being provided by controller 201 as described in various portions of the disclosure.

Figure 16:
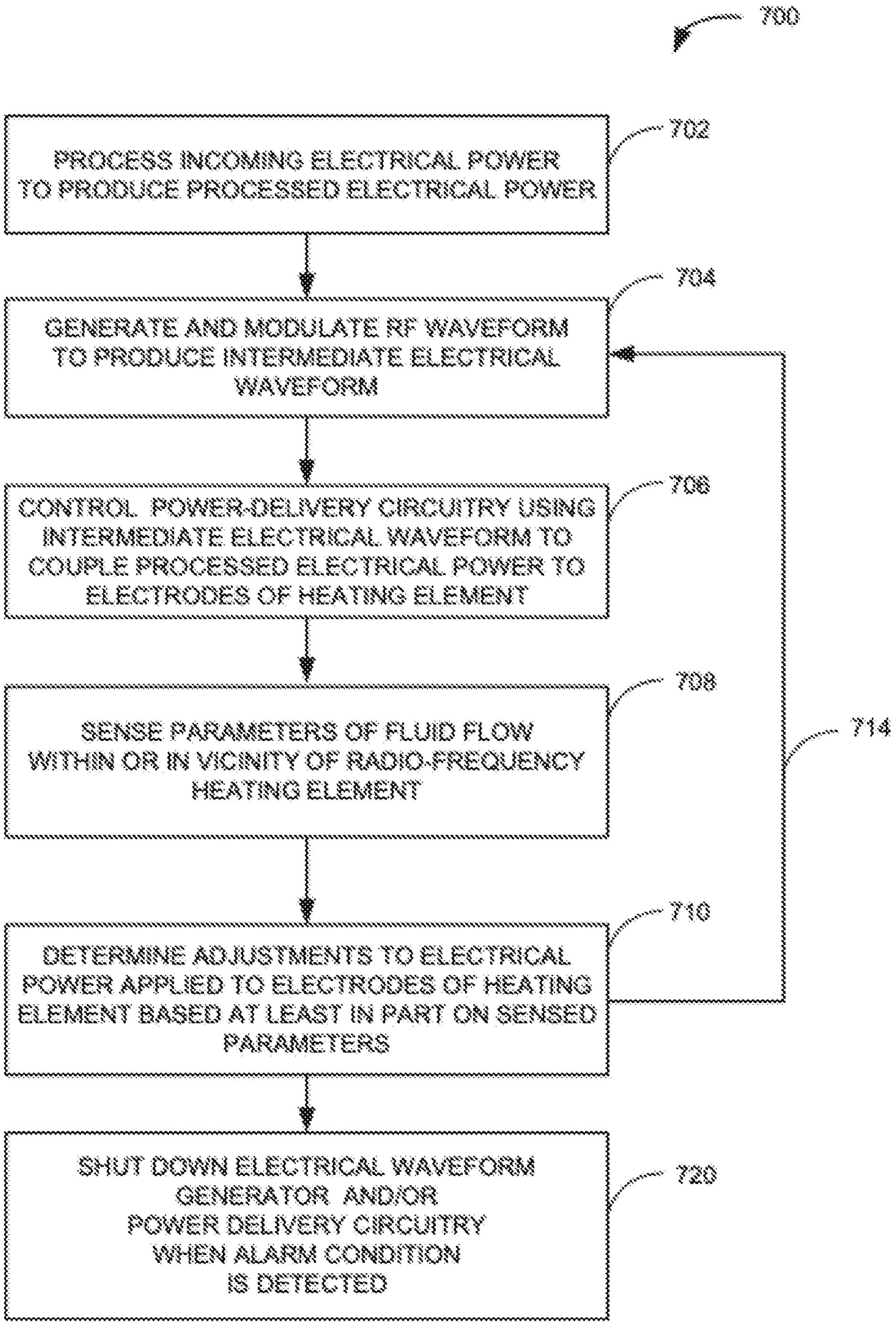
FIG. 16 illustrates a flowchart for a method for non-contact radio-frequency heating control according to at least one embodiment.

FIG. 16 illustrates a flowchart for a method 700 for non-contact radio-frequency heating control according to at least one embodiment. Embodiments of method 700 may utilize one or more, or any combination thereof, of devices and circuitry described above and throughout this disclosure, and any equivalents thereof, to perform the procedures and processes included as part of method 700. One, some, or all of the method steps described below, and any equivalents thereof, may be performed under the control of or based on control signals provided by control circuitry, such as but not limited to control circuitry 210 (FIGS. 13 and 15A) including one or more processors, such as processor 211 (FIGS. 13 and 15A).

Embodiments of method 700 may include processing incoming electrical power to produce processed electrical power (block 702). Processing of electrical power may include rectification, filtering, and voltage, current, and/or phase regulation of incoming electrical power. In various embodiments, processor(s) of the control circuitry may provide control signals, for example to an input power processing circuitry, to modify or control one or more parameters, such as a voltage or a power level provided an output of the electrical power processed and provided as an output from the input power processing circuitry.

Embodiments of method 700 may include generating and modulating an RF waveform to produce an intermediate electrical waveform (block 704). Generation of an RF waveform may be performed by an RF source, such as RF source 204A (FIGS. 13 and 15A), and modulation of the RF waveform to produce the intermediate electrical waveform may be performed by a modulator, such as modulator 204B (FIGS. 13 and 15A). The format and/or other parameters of the intermediate electrical waveform may correspond to any of the formats and may include any of the parameters described throughout this disclosure with respect to intermediate electrical waveforms, and any equivalents thereof.

Embodiments of method 700 may include controlling a power-delivery circuitry using the intermediate electrical waveform to control coupling of the processed electrical power to one or more sets of electrodes of a RF heating element (block 706). In various embodiments, the control provided by power-delivery circuitry may include switching ON and switching OFF the electrical coupling between the processed electrical power being provided to the power-delivery circuitry and the one or more sets of electrodes in order to provide a modulated or a pulsed electrical output waveform to the one or more sets of electrode included in the RF heating element, and thereby control the heating of a fluid flowing through or contained within the heating element. Embodiments of method 700 may include coupling the electrical output waveform from the one or more electrode output terminals of a control unit to one or more sets of electrodes positioned in a non-contact radio-frequency heating element through one or more electrical conductors, such as but not limited to one or more shielded co-axial cables. Providing the electrical output waveform from the one or more electrode output terminals to one or more sets of electrodes positioned in a non-contact radio-frequency heating element may result in a heating of a fluid passing between or contained within an area between the one or more sets of electrodes.

Embodiments of method 700 may include sensing parameters associated with a fluid flowing through and/or contained within the RF heating element (block 708). Sensed parameters may include but are not limited to sensing a temperature of the fluid, sensing a flow rate, or sensing a flow volume associated with the fluid.

Embodiments of method 700 may include determining, for example using control circuitry, adjustments to the electrical power that is/are being applied to the one or more sets of electrodes of the non-contact radio-frequency heating element based at least in part on the sensed parameters (block 710). In various embodiments, a determination of any adjustments to the electrical output waveform(s) is based on one or more sensed temperatures associated with the fluid being heated by the non-contact radio-frequency heating element. In various embodiments, a determination of any adjustments to the electrical output waveform(s) is based on one or more sensed flow rates or a sensed flow volume associated with the fluid being heated by the non-contact radio-frequency heating element.

Based on a determination of any adjustment that may need to be made to the electrical output waveform(s), method 700 returns to block 704, as indicated by return line 714, where further control of the electrical waveform generator and/or the power-delivery circuitry is performed based on any of the adjustments determined to be made at block 710. Heating of the fluid may continue in a loop including blocks 702 through 710 until an operator shuts the control unit that is performing method 700 off, or an alarm condition is detected (block 720).

When an alarm condition is detected, embodiments of method 700 may include shutting down the electrical waveform generator and/or the power-delivery circuitry of the control unit. Alarm conditions can include but are not limited to an over temperature detected for the fluid being heated by the non-contact radio-frequency heating element, an unacceptable condition related to the flow rate or flow volume associated with the fluid being heated by the non-contact radio-frequency heating unit, and/or an electrical or temperature condition associated with the control unit and/or the non-contact radio-frequency heating unit, such as a short circuit, loss of input electrical power to the control unit, and any unacceptable and detected over temperature, overcurrent, or overvoltage condition that might exist within the control unit. In various embodiments, the control unit is configured to output a warning signal, for example through a user interface, to one or more devices located external to the control unit, the warning signal(s) including information related to the detection of an alarm condition, and/or information related to the nature and the extent of the condition that generated the alarm condition.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a “circuit,” “circuitry,” “module,” or “system.” The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine-readable medium may be a machine-readable signal medium or a machine readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain or store a program for use by or in connection with an instruction execution system, apparatus, or device. A machine-readable storage medium is not a machine-readable signal medium.

A first embodiment of the invention includes a method for treating a bleeding nasal passageway wherein an irrigant in the temperature range of 46 degrees Celsius to 52 degrees Celsius is motivated to flow into the first nasal passageway then past the posterior septal margin and through the contralateral nasal passageway and out the contralateral nare for a sufficient period of time and volume to cause hemostasis of the bleeding nasal passageway.

The first embodiment of the invention includes a method wherein the irrigant flow rate is between 2 cc/second and 12 cc/second.

The first embodiment of the invention includes a method wherein the irrigant flow rate is controlled by measuring the volumetric change of the irrigant in an irrigant reservoir.

The first embodiment of the invention includes a method wherein the irrigant flow rate is controlled by increasing or decreasing the rate of irrigant flow through a mechanism.

A second embodiment of the invention includes a device for treating a bleeding nasal passageway wherein the device incudes a reservoir capable of holding or receiving an irrigant, a heating system, temperature controller, irrigant pump, and nasal interface wherein the irrigant is heated by the irrigant heating system to a temperature in the range of 48 degrees Celsius to 52 degrees Celsius and the irrigant is motivated by the irrigant pump to flow into a first nasal passageway and past a bleeding site in the nasal passageway or a contralateral nasal passageway.

The second embodiment of the invention includes a device wherein the irrigant is at a temperature below 48 degrees Celsius and after the flow of irrigant commences, the irrigant heating system raises the temperature of the irrigant to within the range of 48 degrees Celsius to 52 degrees Celsius while it flows into the nasal passageway.

The second embodiment of the invention includes a device wherein the irrigant is motivated by the pump to flow at a rate between 2 cc per second and 12 cc per second.

The second embodiment of the invention includes an aspect wherein the device has two irrigant temperature settings, wherein the first irrigant temperature setting heats the irrigant to a temperature range between 35 degrees Celsius and 46 degrees Celsius and the second heat setting heats the irrigant to within the range of 46 degrees Celsius to 52 degrees Celsius wherein the device causes the irrigant to flow at a controlled rate and at a controlled temperature into first nasal passageway, around the posterior margin of the septum, into the contralateral nasal passageway before exiting the contralateral nare.

The second embodiment of the invention includes an aspect wherein the device heats irrigant to within the temperature range of 35 degrees Celsius and 46 degrees Celsius and after reaching the temperature range, a preset volume of irrigant is induced to flow at a controlled flow rate into a first nasal passageway, around the posterior margin of the septum, into the contralateral nasal passageway, and exits the contralateral nare; then the temperature of the irrigant is increased to within the range of 46 degrees Celsius to 52 degrees Celsius and irrigant at the temperature is induced to flow at a controlled flow rate into a first nasal passageway, around the posterior margin of the septum, into the contralateral nasal passageway and exits the contralateral nare.

The second embodiment of the invention includes an aspect wherein the device heats irrigant to within the temperature range of 35 degrees Celsius and 46 degrees Celsius and after reaching the temperature range, irrigant is induced to flow at a controlled rate for a preset period of time into a first nasal passageway, around the posterior margin of the septum, into the contralateral nasal passageway, and exits the contralateral nare; then the temperature of the irrigant is increased to within the range of 46 degrees Celsius to 52 degrees Celsius and irrigant at the temperature is induced to flow at a controlled rate into a first nasal passageway, around the posterior margin of the septum, into the contralateral nasal passageway and exits the contralateral nare.

The second embodiment of the invention includes an aspect wherein the device has two irrigant flow rate settings, wherein the temperature of the irrigant is in the range between 42 degrees Celsius and 52 degrees Celsius and the first irrigant flow rate is in the range of 2 cc/min to 6 cc/min and the second irrigant flow rate is in the range of 5 cc/min to 12 cc/min wherein the device motivates the irrigant to flow at a controlled rate and at a controlled temperature into first nasal passageway, around the posterior margin of the septum, into the contralateral nasal passageway before exiting the contralateral nare.

The second embodiment of the invention includes an aspect wherein the device motivates a preset volume of irrigant to flow at a first flow rate into a first nasal passageway, around the posterior margin of the septum, into the contralateral nasal passageway, and exits the contralateral nare; then after the preset volume of irrigant has been motivated to flow out of irrigant reservoir, the flow rate of the irrigant is increased to flow at a second flow rate into a first nasal passageway, around the posterior margin of the septum, into the contralateral nasal passageway and exits the contralateral nare.

A third embodiment of the invention includes a device configured to motivate the temperature-controlled irrigant into one nasal passageway then stops the flow of the irrigant prior to the irrigant reaching the posterior margin of the nasal septum, then the irrigant direction is reversed such that it flows out of the same nare that it entered the nasal passageway.

The third embodiment of the invention includes an aspect wherein the device incorporates a valve mechanism to divert the effluent away from the irrigant receptacle. A fourth embodiment of the invention includes a device configured to treat either epistaxis or upper gastrointestinal bleeding using an irrigant to lavage the nasal passageway or the stomach wherein the irrigant temperature is in the range of 46 degrees Celsius to 52 degrees Celsius.

A fifth embodiment of the invention includes a device comprised of a reservoir for containing irrigant, an irrigant heating system, and a temperature control system wherein the reservoir contains irrigant that is heated in the range of 46 degrees Celsius to 52 degrees Celsius and the reservoir is configured with a spout to pour irrigant from the reservoir into the nasal passageway of the patient such that the irrigant flows past a bleeding site in the nasal passageway or a contralateral nasal passageway.

A sixth embodiment of the invention includes a device comprised of a reservoir for containing irrigant, an irrigant heating system, and a temperature control system wherein the reservoir contains irrigant that is heated in the range of 46 degrees Celsius to 52 degrees Celsius and the reservoir may be squeezed to motivate the irrigant into the nasal passageway of the patient such that the irrigant flows past a bleeding site in the nasal passageway or a contralateral nasal passageway.

A seventh embodiment of the invention includes a method for treating gastric bleeding wherein an irrigant in the temperature range of 46 degrees Celsius to 52 degrees Celsius is motivated to lavage a patient's stomach wherein the stomach has one or more bleeding sites and the irrigant flows out of the patient's stomach and flows into a collection receptacle.

An eighth embodiment of the invention includes a device for treating gastric bleeding wherein the device is comprised of a reservoir capable of holding or receiving an irrigant, a heating system, temperature controller, irrigant pump, and nasal interface wherein the irrigant is heated by the irrigant heating system to a temperature in the range of 46 degrees Celsius to 52 degrees Celsius and the irrigant is motivated by the irrigant pump to lavage a patient's bleeding stomach and the irrigant exits the bleeding patient's stomach and flows into a collection receptacle.

A ninth embodiment of the invention includes a method of treating epistaxis using an apparatus that induces the patient to position the head forward then inducing irrigant flow at a controlled temperature and at a controlled rate wherein the irrigant flows into the first nasal passageway, around the posterior margin of the septum, into the contralateral nasal passageway before exiting the contralateral nare.

The ninth embodiment of the invention includes a method wherein the irrigant flow rate is between 2 cc/second and 12 cc/second.

The ninth embodiment of the invention includes a method wherein the temperature of the irrigant is between 46 degrees Celsius and 52 degrees Celsius.

A tenth embodiment of the invention includes a device with two irrigant reservoirs such that irrigant flows in a closed circuit between the two reservoirs wherein the first reservoir contains irrigant that is pumped at a controlled flow rate and at a controlled temperature into the first nasal passageway, past the posterior margin of the septum, then into the contralateral nasal passageway before it flows out the contralateral nare, through tubing and into a second reservoir wherein the second reservoir is fluidly connected to the first reservoir such that as the irrigant flows out of the first reservoir, air from the second reservoir flows into the first reservoir thereby lowering the pressure in the second reservoir thereby inducing the irrigant to flow into the second reservoir after passing through the nasal passageways.

The tenth embodiment of the invention includes an aspect wherein the irrigant flow rate is between 2 cc/second and 12 cc/second.

The tenth embodiment of the invention includes an aspect wherein the temperature of the irrigant is between 46 degrees Celsius and 52 degrees Celsius.

An eleventh embodiment of the invention includes a method for treating bleeding in the urethra wherein an irrigant in the temperature range of 46 degrees Celsius to 52 degrees Celsius is motivated to lavage a patient's urethra via a catheter wherein the irrigant flows to the urethra via the catheter. An aspect of the eleventh embodiment includes a method wherein the irrigant flows from the urethra via the catheter.

The eleventh embodiment of the invention includes an aspect wherein the irrigant flow rate is between 2 cc/second and 12 cc/second.

A twelfth embodiment of the invention includes a system for treating bleeding in a urethra. The system includes an irrigant source, a heating apparatus connected to the irrigant source, wherein the heating apparatus is configured to heat an irrigant as the irrigant flows through the heating apparatus, and a treatment catheter having an irrigant outlet and an irrigant inlet located at a distal portion of a catheter body of the treatment catheter, wherein the irrigant outlet is located farther distally on the catheter body than the irrigant inlet.

The twelfth embodiment includes an aspect wherein the irrigant flow rate is between 2 cc/second and 12 cc/second.

The twelfth embodiment includes an aspect wherein the irrigant temperature is between 46 degrees Celsius and 52 degrees Celsius.

The twelfth embodiment includes an aspect wherein the system includes a pump.

The twelfth embodiment includes an aspect wherein the heating apparatus includes a heating element that heats the irrigant via a volumetric heating method. An aspect of the twelfth embodiment includes heating the irrigant via the application of radio-frequency energy.

The twelfth embodiment includes an aspect wherein the treatment catheter includes one or more sensors configured to sense temperature, flow rate, or other physical variables.

The twelfth embodiment includes an aspect wherein the heating apparatus includes one or more sensors configured to sense temperature, flow rate, or other physical variables.

The twelfth embodiment includes an aspect wherein a controller receives data feedback including temperature, flow rate, or other physical variables from sensors on the treatment catheter and/or the heating apparatus and uses the data feedback to control the heating apparatus.

The twelfth embodiment includes an aspect wherein a controller receives data feedback including temperature, flow rate, or other physical variables from sensors on the treatment catheter and/or the heating apparatus and uses the data feedback to control a pump.

For the purposes of describing and defining the present invention it is noted that the use of relative terms such as "substantially", "generally", "approximately" and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The phrase "in one embodiment" is used repeatedly. The phrase generally does not refer to the same embodiment; however, it may. The terms "comprising," "having" and "including" are synonymous; unless the context dictates otherwise. The following illustrations of various embodiments use particular terms by way of example to describe the various embodiments, but this should be construed to encompass and provide for terms such as "method" and "routine" and the like.

Exemplary embodiments of the present invention are described above. No element, act or instruction used in this description should be construed as important, necessary, critical or essential to the invention unless explicitly described as such. Although only a few of the exemplary embodiments have been described in detail herein and those skilled in the art will readily appreciate that many modifications are possible in these exemplary embodiments without materially departing from the novel teachings and advantages of this invention. Accordingly, all such modifications are intended to be included within the scope of this invention.

TABLE OF REFERENCE NUMBERS

| | |
|---|---|
| 1 | Lid |
| 2 | Reservoir |
| 3 | Switch |
| 4 | Screen |
| 5 | Power cord |
| 6 | Irrigant nozzle |
| 7 | Enclosure |
| 8 | Down button |
| 9 | Up button |
| 10 | Wall |
| 11 | Recirculating inlet |
| 12 | Recirculating impeller |
| 13 | Recirculating impeller nozzle |
| 14 | Main impeller inlet |
| 15 | Temperature sensor |
| 16 | Reservoir base |
| 17 | Heater |
| 18 | Heater wire |
| 19 | Heater wire |
| 20 | Electronic controller |
| 21 | Recirculating impeller shaft |
| 22 | Motor |
| 23 | Main impeller |
| 24 | Irrigant flow rate sensor |
| 25 | Main impeller shaft |
| 26 | Main impeller inlet tube |
| 29 | Irrigant valve |
| 30 | Nozzle interface |
| 31 | Therapy tube lumen |
| 32 | Nasal interface |
| 33 | Tubing wall |
| 34 | Tubing valve |
| 35 | Recirculating impeller shaft |
| 36 | Heater |
| 37 | Recirculating impeller |
| 38 | Main impeller |
| 39 | Main impeller housing |
| 40 | Insulating wall |
| 42 | Exit conduit |
| 43 | Main impeller inlet |
| 44 | Reservoir |
| 45 | Vent tube |
| 46 | Stopcock |
| 47 | Temperature sensor |
| 48 | Temperature controller |
| 49 | Motor |
| 50 | Irrigant source |
| 55 | Source tubing |
| 65 | Delivery tubing |
| 75 | Pump |
| 100 | Treatment catheter |
| 110 | Anchoring member |
| 120 | Catheter body |
| 124 | Catheter body distal portion |
| 128 | Catheter body proximal portion |
| 130 | Distal outlet |
| 135 | Distal inlet |
| 140 | Proximal inlet |
| 145 | Proximal outlet |
| 150 | Anchor activation lumen |
| 160 | Supply lumen |
| 170 | Drainage lumen |
| 200 | System |
| 201 | Control unit |
| 202 | Electrical power input lines |
| 203 | Input power processing circuitry |
| 204 | Waveform generator |
| 204A | RF source |
| 204B | Modulator |
| 205 | Power-delivery circuitry |
| 206 | Electrode output terminal |
| 207 | Electrode return terminal |
| 208 | Electrode conductors wiring (conductors) |
| 209 | Arrow |
| 210 | Control circuitry |
| 211 | Processor(s) |
| 212 | Memory |
| 214 | User interface |
| 216 | Temperature output |
| 218 | Sensor inputs |
| 219 | Multiplexer |
| 220 | Power line(s) |
| 250 | Element |
| 251 | Body |
| 252 | Passageway |
| 253 | Fluid input conduit |
| 254 | Fluid output conduit |
| 255 | Electrode |
| 256 | Return electrode |
| 257 | Temperature sensor(s) |
| 258 | Sensor input lines |
| 259 | Flow sensor |
| 260 | Fluid source/pump |
| 261 | Distance between electrodes |
| 262 | Longitudinal axis - heating element |
| 263 | Length dimension - heating element |
| 264 | Ambient temperature sensor(s) |
| 265 | Computer system |
| 270 | Element |
| 271 | Body |

-continued

| TABLE OF REFERENCE NUMBERS | |
|---|---|
| 272 | Outer tube |
| 273 | Inner tube |
| 274 | Length dimension |
| 276 | First end |
| 277 | Second end |
| 278 | Passageway |
| 281 | Inductive coil |
| 282 | Inductive coil |
| 283 | Inductive coil |
| 284 | Inductive coil |
| 300 | Heating apparatus |
| 301 | Waveform |
| 302 | Vertical axis |
| 303 | Horizontal axis |
| 304 | Variable line double arrows |
| 305 | First time period - arrow |
| 306 | Overall period - arrow |
| 307 | Second time period - arrow |
| 308 | Variable line double arrows |
| 310 | Subsequent time period - ON cycle |
| 311 | Subsequent time period - OFF cycle |
| 312 | Additional switching cycles |
| 331 | Electrical output waveform |
| 332 | Vertical axis |
| 333 | Horizontal axis |
| 335 | First time period - arrow |
| 336 | Variable line double arrows |
| 337 | Second time period - arrow |
| 338 | Variable line double arrows |
| 340 | Dashed line - voltage ramp |
| 341 | Dashed line - voltage ramp |
| 350 | Heating element |
| 351 | Power source |
| 352a | First side plate |
| 352b | Second side plate |
| 355a | Electrode |
| 355b | Electrode |
| 358 | Fluid passageway |
| 361 | Electrical output waveform |
| 362 | Vertical axis |
| 363 | Horizontal axis |
| 365 | First time period - arrow |
| 366 | Variable line double arrows |
| 367 | Second time period - arrow |
| 368 | Variable line double arrows |
| 400 | System |
| 401 | Electrode output terminal 1 |
| 402 | Electrode output terminal 2 |
| 403 | Electrode output terminal 3 |
| 404 | Electrode output terminal 4 |
| 411 | Electrode 1 |
| 412 | Electrode 3 |
| 413 | Electrode 4 |
| 414 | Electrode 5 |
| 420 | Return electrode |
| 422 | Electrode conductor wiring (conductors) |
| 560 | Liner |
| 562 | Outer surface |
| 564 | Connection surface |
| 568 | Liner cavity |
| 700 | Method |
| 702 | Method block |
| 704 | Method block |
| 706 | Method block |
| 708 | Method block |
| 710 | Method block |
| 714 | Return line |
| 720 | Method block |

We claim:

1. A system for treating internal bleeding, comprising:

a reservoir configured to hold an irrigant;

a first impeller disposed within the reservoir, and configured to recirculate the irrigant within the reservoir;

a second impeller disposed within the reservoir and configured to motivate the irrigant from the reservoir;

a motor that simultaneously spins both the first impeller and the second impeller;

a heating element configured to heat the irrigant to generate a heated irrigant as the irrigant flows through and recirculates within the reservoir, wherein the heated irrigant is configured to arrest the internal bleeding upon delivery of the heated irrigant to a treatment area; and a treatment catheter configured to receive the heated irrigant from the reservoir, the treatment catheter having an irrigant outlet and an irrigant inlet located at a distal portion of a catheter body of the treatment catheter, wherein the irrigant outlet is located farther distally on the catheter body than the irrigant inlet;

wherein the system is configured to deliver the heated irrigant from the irrigant outlet to the treatment area where there is the internal bleeding such that the heated irrigant is delivered at a flow rate of between 2 cc/s and 12 cc/s and a temperature of between 46 degrees Celsius and 52 degrees Celsius.

2. The system of claim 1 wherein the heating element is configured to heat the irrigant via volumetric heating.

3. The system of claim 1 wherein the heating element is configured to heat the irrigant via application of radiofrequency energy.

4. The system of claim 1 wherein the treatment catheter, the heating element, or both include one or more sensors.

5. The system of claim 4 further comprising a controller, wherein the controller is configured to receive data feedback from the one or more sensors.

6. The system of claim 5 wherein the controller controls the heating element using the data feedback.

7. The system of claim 5, wherein the controller controls the motor using the data feedback.

8. The system of claim 1 wherein the flow rate is between 2 cc/s and 6 cc/s.

9. The system of claim 1 wherein the temperature is between 48 degrees Celsius and 52 degrees Celsius.

10. The system of claim 1, wherein the second impeller is configured to motivate the heated irrigant from the reservoir into the treatment catheter.

11. A system for treating internal bleeding, comprising:

a treatment catheter having an irrigant outlet and an irrigant inlet located at a distal portion of a catheter body of the treatment catheter, wherein the irrigant outlet is located farther distally on the catheter body than the irrigant inlet; and a heating apparatus connected the treatment catheter, wherein the heating apparatus includes:

a reservoir configured to hold an irrigant;

a first impeller disposed within the reservoir and configured to recirculate the irrigant within the reservoir;

a second impeller disposed within the reservoir and configured to motivate the irrigant from the reservoir into the treatment catheter;

a motor that simultaneously spins both the first impeller and the second impeller; and a heating element configured to heat the irrigant to a temperature suitable to arrest the internal bleeding as the irrigant flows through the heating element to the treatment catheter;

wherein the system is configured to deliver heated irrigant from the irrigant outlet to a treatment area where there is the internal bleeding such that the heated irrigant is delivered at a flow rate of between 2 cc/s and 12 cc/s and at a temperature of between 46 degrees Celsius and 52 degrees Celsius.

* * * * *